US010067079B2

(12) United States Patent
Chi et al.

(10) Patent No.: US 10,067,079 B2
(45) Date of Patent: Sep. 4, 2018

(54) SOLID STATE NMR SPECTROSCOPY/IMAGING IN SITU MEASURING DEVICES AND METHODS FOR CALIBRATION AND DETERMINING ONE OR MORE QUANTITATIVE PROPERTIES OF A TARGET SAMPLE

(71) Applicant: The Curators of the University of Missouri, Columbia, MO (US)

(72) Inventors: Lingyu Chi, Rolla, MO (US); Ming Huang, Rolla, MO (US); Rex E. Gerald, II, Rolla, MO (US); Klaus Woelk, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 371 days.

(21) Appl. No.: 14/941,372

(22) Filed: Nov. 13, 2015

(65) Prior Publication Data

US 2016/0109391 A1  Apr. 21, 2016

Related U.S. Application Data

(63) Continuation-in-part of application No. 14/884,686, filed on Oct. 15, 2015.
(Continued)

(51) Int. Cl.
*G01N 24/08* (2006.01)
*G01R 33/00* (2006.01)
(Continued)

(52) U.S. Cl.
CPC ......... *G01N 24/08* (2013.01); *G01R 33/0052* (2013.01); *G01R 33/4804* (2013.01); *G01R 33/307* (2013.01); *G01R 33/31* (2013.01)

(58) Field of Classification Search
CPC ..... G01R 33/31; G01R 33/46; G01R 33/0052
See application file for complete search history.

(56) References Cited

U.S. PATENT DOCUMENTS 3,630,191 A      12/1971   Gilford
4,510,450 A  *   4/1985    Brown ................ G01R 33/307
                                                               324/308

(Continued)

OTHER PUBLICATIONS

International Search Report with Written Opinion dated Feb. 3, 2017 in International Patent Application No. PCT/US16/61551, 12 pages.

*Primary Examiner* — Huy Q Phan
*Assistant Examiner* — Dustin Dickinson
(74) *Attorney, Agent, or Firm* — Shook, Hardy & Bacon L.L.P.

(57) ABSTRACT

In situ measuring devices, methods of making the same, and methods of using the same are provided herein. The in situ measuring devices can include a capillary tube having a reference material sealed inside the capillary tube, where the capillary tube is positioned inside of a solid state or MAS NMR rotor. A target sample can also be positioned in the interior of the solid state or MAS NMR rotor but is sequestered from the reference material by a capillary tube wall. The in situ measuring devices can be used in solid state MAS NMR spectroscopy to quantify one or more parameters of a target sample, such as the quantity of a sample, chemical identity of a sample, or temperature of a sample.

20 Claims, 22 Drawing Sheets

Related U.S. Application Data

(60) Provisional application No. 62/123,327, filed on Nov. 14, 2014, provisional application No. 62/137,057, filed on Mar. 23, 2015, provisional application No. 62/122,235, filed on Oct. 15, 2014.

(51) Int. Cl.
*G01R 33/48* (2006.01)
*G01R 33/30* (2006.01)
*G01R 33/31* (2006.01)

(56) References Cited

U.S. PATENT DOCUMENTS

| | | |
|---|---|---|
| 6,054,857 A | 4/2000 | Doty |
| 7,397,241 B2 | 7/2008 | Gauthausen et al. |
| 8,367,028 B2 | 2/2013 | Lemon et al. |
| 2005/0024055 A1* | 2/2005 | Cavaluzzi ............. G01R 33/30 324/321 |
| 2008/0007262 A1* | 1/2008 | Yamauchi ............ G01R 33/307 324/309 |
| 2008/0297157 A1 | 12/2008 | Hu et al. |
| 2010/0156414 A1* | 6/2010 | Sakellariou ......... G01R 33/307 324/309 |
| 2010/0260665 A1 | 10/2010 | Archer et al. |
| 2011/0080171 A1* | 4/2011 | Takegoshi ............ G01R 33/307 324/318 |
| 2014/0005033 A1 | 1/2014 | Ghosh |
| 2014/0081014 A1 | 3/2014 | Yaghi et al. |
| 2016/0109391 A1 | 4/2016 | Chi et al. |

\* cited by examiner

| SPINNING SPEED | DISTANCE | TEMPERATURE |
|---|---|---|
| 14 kHz | 1.39 ppm | 325.78 K |
| 10 kHz | 1.56 ppm | 308.72 K |
| 6 kHz | 1.65 ppm | 299.69 K |
| 2 kHz | 1.7 ppm | 294.67 K |
| 0.5 kHz | 1.72 ppm | 292.67 K |

SOLID STATE NMR SPECTROSCOPY/IMAGING IN SITU MEASURING DEVICES AND METHODS FOR CALIBRATION AND DETERMINING ONE OR MORE QUANTITATIVE PROPERTIES OF A TARGET SAMPLE

CROSS-REFERENCE TO RELATED APPLICATIONS

This application is a continuation-in-part of U.S. application Ser. No. 14/884,686, filed on Oct. 15, 2015, entitled "In Situ NMR Parameter Monitoring Systems and Methods for Measuring PH and Temperature," which claims priority to U.S. Provisional Application 62/122,235 filed on Oct. 15, 2014, entitled "In Situ NMR Thermometer," and to U.S. Provisional Application 62/137,057 filed on Mar. 22, 2015, entitled "In Situ pH Meter," both of which are incorporated in their entireties herein, and this application claims priority to U.S. Provisional Application 62/123,327, filed on Nov. 14, 2014, entitled "Calibration CapPack Devices for Magic Angle Spinning (MAS) NMR Experiments," which is incorporated in its entirety herein.

GRANT STATEMENT

None.

FIELD OF THE INVENTION

The present disclosure relates to the field of NMR spectroscopy/imaging, and more specifically, to in situ measuring devices for calibration and determining one or more quantitative properties of a target sample.

BACKGROUND

Certain conventional electronic devices are commercially available for monitoring intensive properties of NMR samples, such as an electronic pH meter that measures pH values for NMR samples by installing a sensor at the tip of a long, small-diameter rod and positioning such sensor inside an NMR tube, e.g., a 5 mm NMR tube. However, such a conventional device and technique requires the removal of the NMR tube from the NMR probe in order to measure the pH value of the sample. Removing an NMR tube for this purpose is inconvenient when monitoring chemical reactions by in situ NMR spectroscopy, especially when the pH changes unexpectedly and rapidly throughout the course of the reaction. Further, other conventional devices for monitoring NMR samples, such as an NMR temperature probe require placing the device in the probe, making a series of NMR measurements at different probe temperature settings, making a series of corresponding probe temperature measurements with an independent thermocouple or other electronic temperature sensor, removing the device from the probe, and creating a calibration curve. The NMR sample to be analyzed is then placed in the probe, the probe temperature setting is adjusted to a desired value, the NMR sample is allowed to equilibrate to the probe temperature, and the calibration curve is used to predict the temperature of the NMR sample. The explicit assumption is that the calibration curve provides an accurate prediction of the temperature of the NMR sample. It is often the case that the assumption is invalid and that the predicted temperature of the NMR sample is erroneous. Additionally, the conventional device is costly and the procedure for measuring and assigning the temperature of the NMR sample is extensive, tedious, time-consuming, and inherently prone to operator error. Furthermore, the numerical value of temperature that is assigned to the corresponding recorded NMR spectrum lacks incipient integrity and, therefore, can be called into question in legal proceedings.

SUMMARY OF THE INVENTION

A high-level overview of various aspects of the invention is provided here for that reason, to provide an overview of the disclosure and to introduce a selection of concepts that are further described below in the detailed description section below. This summary is not intended to identify key features or essential features of the claimed subject matter, nor is it intended to be used as an aid in isolation to determine the scope of the claimed subject matter.

In an exemplary aspect, a device is provided for in situ pH monitoring of a sample using NMR spectroscopy. The device comprises a sample housing member configured to house a target sample, at least one pH sensor configured to exhibit an NMR spectral change due to a change in pH value of the target sample, and a pH sensor containment member configured to house the at least one pH sensor. The pH sensor containment member is positioned inside at least a portion of the sample housing member. Further, at least a portion of the pH sensor containment member comprises one or more pores, which are configured to allow diffusion of hydronium cations and hydroxide anions.

In another exemplary aspect, a method is provided for measuring a pH of a sample in situ using NMR spectroscopy. The method comprises providing an in situ NMR pH measurement device. The device includes a sample housing member configured to house a target sample, at least one pH sensor configured to exhibit an NMR spectral change due to a change in pH value of the target sample, and a pH sensor containment member configured to house the at least one pH sensor. The method further comprises adding the target sample to the sample housing member, obtaining one or more NMR spectra, and determining the pH of at least a portion of the target sample.

In another exemplary aspect, a device is provided for monitoring a temperature of a sample in situ using NMR spectroscopy. The device comprises an NMR sample tube and at least one capillary tube positioned inside the NMR sample tube. The at least one capillary tube is configured to house a reference material. Further, the device comprises a glass seal at a first end and at a second end of the at least one capillary tube that seals the first end and second end after the reference material has been added.

In another exemplary aspect, a method is provided for measuring a temperature of a sample in situ using NMR spectroscopy. The method comprises providing an in situ NMR temperature measurement device. The device includes an NMR sample tube and at least one capillary tube positioned inside the NMR sample tube. The at least one capillary tube is configured to house a reference material and be sealed once the reference material has been added. The method further comprises adding the target sample to the NMR sample tube, obtaining one or more NMR spectra, and determining the temperature of at least a portion of the target sample based on at least one NMR spectrum of the reference material.

Still yet, in another exemplary aspect, a method is provided for forming a seal at one or both ends of a capillary tube used in an in situ NMR temperature measurement device. The method comprises providing at least one capillary tube used in the in situ NMR temperature measurement device, adding a reference material to at least a portion of the at least one capillary tube, and using an Optical Fiber Arc Fusion Splicer to seal a first end of the at least one capillary tube.

In a further exemplary aspect there is provided a method for performing one or more quantitative measurements of a target sample using solid state MAS NMR spectroscopy. The method includes providing an in situ measuring device, the in situ measuring device including a solid state MAS NMR rotor and at least one sealed capillary tube positioned inside the solid state MAS NMR rotor. The at least one sealed capillary tube having a reference material sealed inside the at least one capillary tube. A target sample is positioned on the inside of the solid state MAS NMR rotor. The method further includes obtaining MAS NMR spectra of the target sample and the reference material; and determining one or more quantitative properties of the target sample. The one or more quantitative properties include one or more of a quantity of the target sample, a chemical identity of the target sample, or a temperature of the target sample.

In yet another exemplary aspect there is provided a method for performing one or more quantitative measurements of a target sample using solid state MAS NMR spectroscopy. The method includes providing an in situ measuring device, the in situ measuring device including a solid state MAS NMR rotor and at least one sealed capillary tube positioned inside the solid state MAS NMR rotor, the at least one sealed capillary tube having a reference material sealed inside the at least one capillary tube. A target sample is positioned on the inside of the solid state MAS NMR rotor. The method also includes inserting the in situ measuring device inside a probe of a solid state MAS NMR instrument. In addition, the method includes, while the in situ measuring device is positioned inside a probe of a solid state MAS NMR instrument, obtaining MAS NMR spectra of the target sample and the reference material, where at least one MAS NMR spectral peak associated with the reference material is spaced apart from at least one MAS NMR spectral peak associated with the target material. The method also includes determining one or more of a quantity of the target sample or a chemical identity of the target sample based on the MAS NMR spectra of the target sample and the reference material.

In another exemplary aspect there is provided a method for forming an in situ measuring device for solid state MAS NMR spectroscopy. The method includes providing at least one capillary tube and adding at least one reference material to an inside cavity of the at least one capillary tube. The method also includes sealing one or more ends of the at least one capillary tube to form at least one sealed capillary tube having the at least one reference material inside and providing a solid state MAS NMR rotor, the solid state MAS NMR rotor configured to house a target sample. In addition, the method includes positioning the at least one sealed capillary tube inside the solid state MAS NMR rotor.

BRIEF DESCRIPTION OF THE DRAWINGS

Illustrative embodiments of the present invention are described in detail below with reference to the attached drawing figures, and wherein.

DETAILED DESCRIPTION

The subject matter of select embodiments of the present invention is described with specificity herein to meet statutory requirements. However, the description itself is not intended to define what we regard as our invention, which is what the claims do.

Overview

Various embodiments described herein include systems and methods for the in situ monitoring of one or more intensive properties of an NMR sample.

In Situ pH Sensor

In one or more embodiments, an in situ pH measuring device can be utilized to measure pH of a sample, or sample environment, in a continuous fashion while observing and/or measuring the NMR spectrum of that sample. The in situ pH measuring device is capable of measuring the pH of an NMR sample in situ that is simple to implement and that encodes and affixes an imprimatur of the measured value of the pH in the NMR spectrum, affording inseparability of the pH and the NMR data and incipient integrity of same.

Figure 1A:
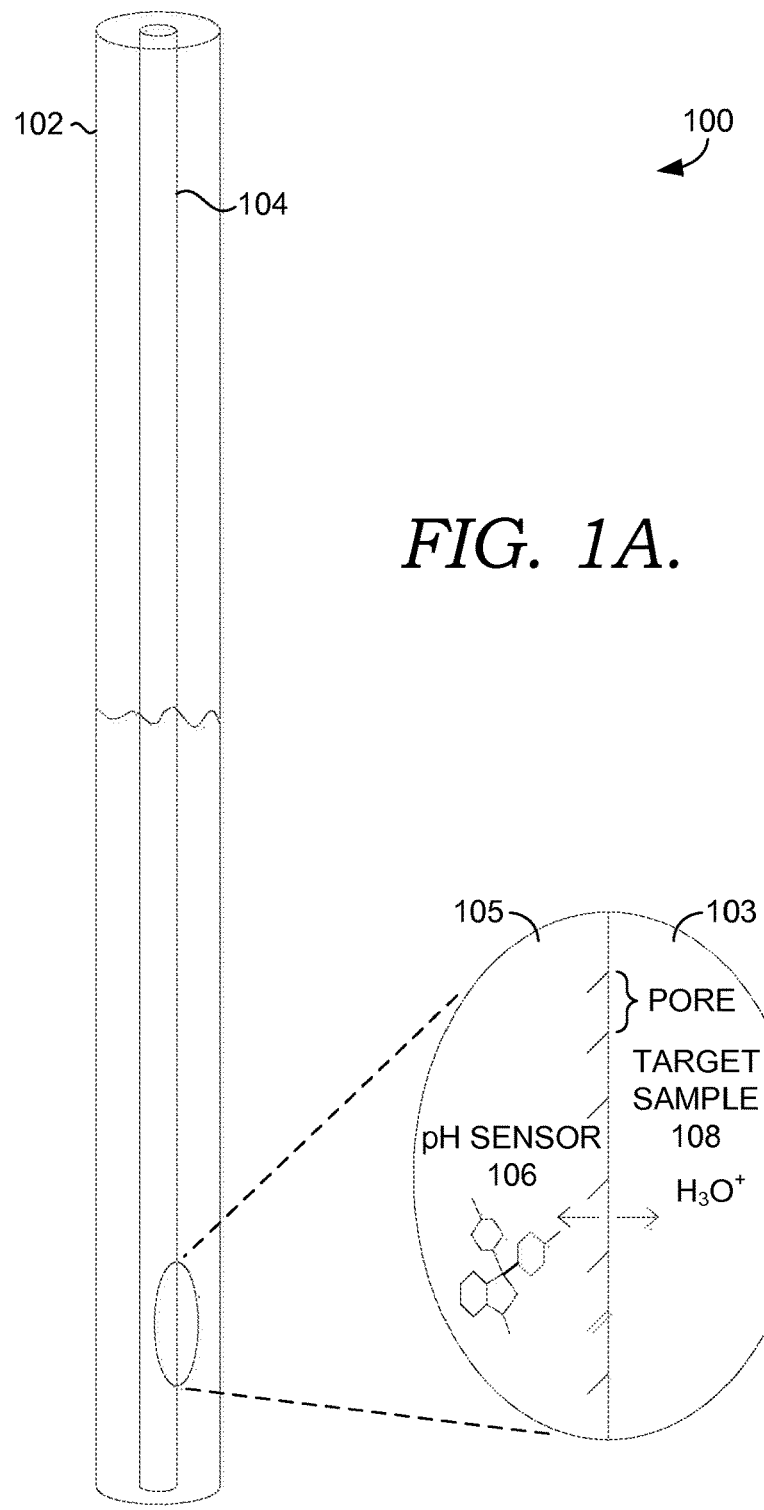
FIG. 1A depicts an in situ pH measuring device, according to one embodiment described herein.
Figure 1B:
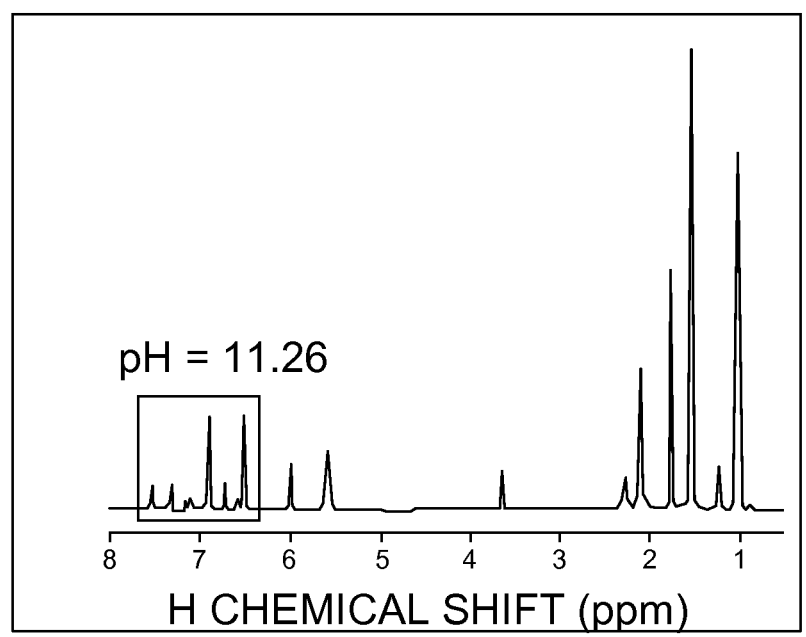
FIG. 1B depicts example NMR spectra that includes the spectral imprint of the in situ pH sensor in the same raw data output NMR spectra of a target sample, according to one embodiment described herein.

One embodiment of an in situ pH measuring device 100 is depicted in FIG. 1A. In embodiments, the in situ pH measuring device 100 can determine pH values of a target sample from a peak or peaks of a spectral pH imprimatur (NMR peaks of a pH sensor molecule which are "embedded" within the NMR spectrum of the sample solution/environment). For example, an example NMR spectra shown in FIG. 1B shows the spectral imprint from the pH sensor molecule (in the box) that is in the same output raw data spectra from the NMR sample.

Unlike a conventional NMR pH meter requiring a user to take out the sample to measure the pH value of a solution contained in a 5-mm NMR tube, the in situ pH measuring device described herein can monitor the pH of a solution while the sample is inside the NMR magnet. Thus, the in situ pH measuring device described herein can be employed to monitor the pH values of a sample solution during the course of a reaction.

The device 100 of FIG. 1 may include a sample housing member 102 and a pH sensor containment member 104 positioned inside of the sample housing member 102. The containment member 104 can be positioned inside of the sample housing member 102 using any techniques known to one skilled in the art, such as one or more annular spacers.

The sample housing member 102 may be any structure suitable for use in NMR and/or MRI that can accommodate a pH sensor containment member. In one embodiment, the sample housing member 102 may be a conventional, commercially available NMR tube, such as a 5 mm outer diameter NMR borosilicate glass tube having a length of about 17 cm. In one or more embodiments, the sample housing member 102 can have an outer diameter of at least about 1 mm, about 2 mm, or about 4 mm, and/or less than about 20 mm, about 15 mm, or about 10 mm.

In embodiments, the sample housing member 102 may define a volume such that a target sample 108 in a preselected sample solution, volume, and/or environment can be positioned in the interior 103 of the sample housing member 102. In the same or alternative embodiments, the pH sensor containment member 104 may define a volume such that a pH sensor 106 can be positioned in the interior 105 of the containment member 104.

In various embodiments, the pH sensor containment member 104 may include various structures and/or materials to provide an interface allowing for the interaction of the pH sensor 106 with hydronium cations and/or hydroxide anions present in the target sample 108 or in the sample housing member 102, but precluding physicochemical interactions between the pH sensor 106 and the target sample 108, e.g., by physically sequestering the pH sensor 106 from direct interaction with the target sample 108. In certain embodiments, the containment member 104 may be a capillary tube with porous walls, e.g., nano-porous walls, having a desired porosity, or a capillary tube with microscopic cracks or fissures. In such embodiments, the desired porosity or the microscopic size or location of the cracks/fissures of the containment member 104 can allow for the bidirectional passage of only small molecules, such as the hydronium cations and/or hydroxide anions. For example, in certain embodiments, the containment member 104 may include pores sized to allow hydronium cations and/or hydroxide anions to diffuse from the sample housing member 102 to the pH sensor containment member 104.

In one or more embodiments, the maximum opening of one or more pores, cracks, and/or fissures present on at least a portion of the containment member 104 to allow for the bidirectional passage of hydronium cations and/or hydroxide anions may be at least about 0.2 Angstroms, at least about 0.3 Angstroms, at least about 0.5 Angstroms, or at least about 1 Angstroms; and/or not more than about 5 Angstroms, not more than about 4 Angstroms, not more than about 3 Angstroms, or not more than about 2 Angstroms. One non-limiting example of a containment member 104 may be a porous VYCOR® capillary tube.

In the one or more embodiments, the containment member 104 may include an interface material, such as any high surface area fiber or thin rod that can tether or entrap pH sensor molecules thereto. In such embodiments, a tethered pH sensor molecule may not be free to diffuse and mix with molecules in the target sample 108 because it is tethered to a fiber; however, such a tethered pH sensor molecule should be chemically inert or innocuous towards the target sample 108, as it may contact the tethered pH sensor molecules.

In certain embodiments, the pH sensor containment member 104 may include a pH sensor 106. In one or more embodiments, the pH sensor 106 exhibits one or more of the following properties: the pH sensor is larger than hydronium ions and/or hydroxide ions so that it may be trapped in a pH sensor containment member 104 while such ions could freely diffuse in and out of the containment member 104; the pH sensor changes structure with a change in pH; the pH sensor can produce NMR signals; the pH sensor can produce NMR signals from nuclei other than the nuclei that produce the NMR spectrum of the target sample; and the pH sensor incorporates nuclei (e.g., $^2$D, $^{12}$C, $^{19}$F, $^{14}$N) into their architecture to make them invisible in the NMR spectrum of the target sample. This last property means that the pH sensor molecule can substitute some of these "dark" nuclei for protons in the pH sensor molecule architecture so that a proton NMR spectrum of the sample under investigation will not include proton signals from the pH sensor molecule.

The pH sensor 106 may include any molecule or ion entity that exhibits a change in particular (or predetermined) concentration as a well-defined function of pH. For example, a change in molecule or ion entity concentration may produce, in direct or other proportion, an NMR and/or MRI detectable change in signal intensity and integral.

In various embodiments, the pH sensor 106 may be of any molecule or ion entity that exhibits a change in the peak volume and/or peak height, or change in chemical shift of one or more nuclear constituents of these entities as a well-defined function of pH. For example, a change in electronic structure of a molecule or ion entity may produce a single-valued NMR and/or MRI detectable change in proton signal chemical shift. In one embodiment, the pH sensor 106 may be unreactive to the target sample 108. In alternative embodiments, the pH sensor may be reactive with the target sample 108.

In one or more embodiments, various molecular and/or ion entities that exhibit an NMR spectral change due to a change in pH may be employed as the pH sensor 106. The changes induced by pH may be in terms of spectral peak volume or chemical shift, whereas the changes may be well-defined/well-calibrated and not interfering with the spectral information of the target sample. In certain embodiments, multiple pH sensors may be employed simultaneously to monitor the pH changes during the course of a reaction. A non-limiting list of commercially available pH sensors with chemical shifts inducible by pH over a certain pH range includes: thymol blue (4-[9-(4-hydroxy-2-methyl-5-propan-2-yl-phenyl)-7,7-dioxo-8-oxa-7λ6-thiabicyclo [4.3.0]nona-1,3,5-trien-9-yl]-5-methyl-2-propan-2-yl-phenol) (pH range of 1.2-2.8); methyl orange (Sodium 4-[(4-dimethylamino)phenyldiazenyl]benzenesulfonate) (pH range of 3.1-4.4); methyl red (2-(N,N-dimethyl-4-aminophenyl)azobenzenecarboxylic acid) (pH range of 4.4-6.2); lithmus (pH range of 5-8); bromothymol blue (4,4'-(1,1-dioxido-3H-2,1-benzoxathiole-3,3-diyl)bis(2-bromo-6-isopropyl-3-methylphenol) (pH range of 6-7.6); BCECF Acid (2',7'-Bis-(2-Carboxyethyl)-5-(and-6)-Carboxyfluorescein) (pH range 6.1-8); thymol phthalein (3,3-bis(4-hydroxy-2-methyl-5-propan-2-ylphenyl)-2-benzofuran-1-one) (pH range of 9.3-10.5); and 4-mercaptobenzoic acid (pH range of 2.5-11). It is appreciated that one skilled in the art would understand how to choose a particular pH sensor and how to prepare it (e.g., prepare a solution comprising a specific concentration of the pH sensor that is applicable to measuring the pH of a sample of interest).

In operation, in certain embodiments, a solution comprising a pH sensor 106 can be placed inside of the pH sensor containment member 104 and placed inside the sample housing member 102, e.g., by using one or more annular spacers. Further, in such embodiments, a target sample can be added to the inside of the annular volume between the outside wall of the pH sensor containment member 104 and the inside wall of the sample housing member 102. In such embodiments, standard NMR and/or MRI analyses known by those skilled in the art may be performed on this double tube assembly. In embodiments, when NMR analyses are applied, the resulting proton NMR signals that emanated from the target sample 108 and the pH sensor 106 may be recorded simultaneously and synchronously by the NMR spectrometer and can be inextricably comingled in the raw data structure, the free induction decay (FID). In such embodiments, a fast Fourier transform (FFT) protocol may be applied to the FID to generate a proton NMR spectrum of the target sample 108 and the pH sensor 106.

In embodiments, in order to generate pH information, a calibration curve can be utilized. In such embodiments, the calibration curve can be composed of a plot of independently, electronically measured pH versus the corresponding NMR parameter (e.g., peak intensity, peak integral, peak chemical shift, spin-lattice relation, spin-spin relaxation). Further in such embodiments, a mathematically-defined curve specific to each sensor molecule is constructed. For example, for a peak intensity NMR parameter measurement, one could select a peak in the $^1$H NMR spectrum of the pH-active molecule, measure and map the peak intensity as a function of independently, electronically-measured pH, use a mathematical function to fit the data, and use the mathematical correlation function to calculate the pH from the $^1$H NMR peak intensity of the pH sensor molecule, and correct pH for temperature variation.

In embodiments utilizing a chemical shift NMR parameter measurement, one could select a peak in the $^1$H NMR spectrum of the pH-active molecule, select another peak from an additionally incorporated nucleus (e.g., $^2$D, $^{13}$C, $^{19}$F, $^{15}$N) as a chemical shift reference observed in a second NMR probe channel, measure and map the relative peak chemical shift, which corresponds to the chemical shift difference from an NMR peak observed in the second NMR probe channel (used a chemical shift reference), as a function of independently, electronically-measured pH, use a mathematical function to fit the data, and use the mathematical correlation function to calculate the pH from the $^1$H NMR peak chemical shift of the pH sensor molecule, and correct pH for temperature variation.

In embodiments utilizing a spin-spin NMR parameter measurement, one could select a peak in the $^1$H NMR spectrum of the pH-active molecule, measure and map spin-spin relaxation rate or time constant as a function of independently, electronically-measured pH, use a mathematical function to fit the data, and use the mathematical correlation function to calculate the pH from the $^1$H NMR peak spin-spin relaxation time constant of the pH sensor molecule, and correct pH for temperature variation.

In Situ NMR Thermometer

As discussed above, various embodiments herein describe an in situ thermometer that can be used in an NMR and/or MRI machine. In one or more embodiments, a device for monitoring actual temperature of a sample in situ with a temperature imprimatur encoded onto the NMR spectrum for accurately determining the thermal properties of the target sample is described. The in situ NMR thermometer described herein is capable of measuring the temperature of an NMR sample in situ and is simple to implement and that encodes and affixes an imprimatur of the measured value of the temperature in the NMR spectrum, affording inseparability of the temperature and the NMR data and incipient integrity of same.

In certain embodiments, the temperature measuring device may include one or more capillary tubes containing a reference material, where such tube(s) is/are centrally or spatially arranged in a sample tube (for solution sample) or a rotor (for solid sample). Any or all tubes may be sealed or unsealed. In embodiments, as discussed below, one or more of the capillary tubes may be sealed using a flame or plasma arc.

Figure 2:
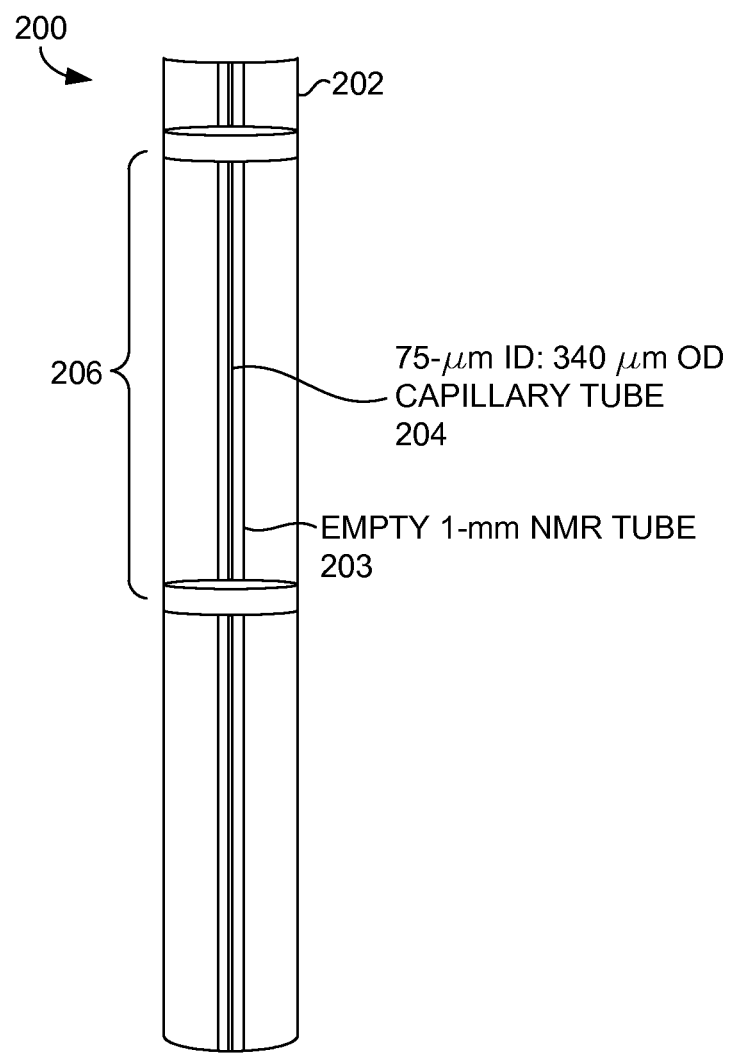
FIG. 2 depicts an in situ NMR thermometer, according to one embodiment described herein.

FIG. 2 shows one embodiment of a temperature measuring device 200. The temperature measuring device 200 can include an NMR tube 202, e.g., a 5 mm coaxial sample 400 MHz J-Young tube, with a smaller inner NMR tube 203, e.g., a conventional 1 mm NMR tube positioned inside of the NMR tube 202. In the temperature measuring device 200 of FIG. 2, a capillary tube 204 can be positioned inside the smaller inner NMR tube 203. The smaller inner NMR tube 203 and/or the capillary tube 204 can be secured inside the NMR tube 202, e.g., by annular spacers 206. In embodiments, the smaller inner NMR tube 203 is empty besides the inserted capillary tube 204, while the NMR tube 202 contains the target sample.

The capillary tube 204 may be configured to house a reference material for the measurement of temperature. In embodiments, the capillary tube 204 can be about 152 mm in length. In one embodiment, the capillary tube 204 can have an outer diameter of at least about 100 micrometers, about 200 micrometers, or about 300 micrometers, and/or an outer diameter of less than about 600 micrometers, 500 micrometers, or 400 micrometers. In certain embodiments, the capillary tube 204 can have an outer diameter of about 340 micrometers. In the same or alternative embodiments, the capillary tube 704 can have an internal diameter of at least about 2 micrometers, about 5 micrometers, about 10 micrometers, about 20 micrometers, about 30 micrometers, 40 micrometers, or 50 micrometers, and/or an internal diameter of less than about 150 micrometers, 125 micrometers, or 100 micrometers. In one embodiment, the capillary tube 204 can have an internal diameter of about 75 micrometers.

In various embodiments, the capillary tube 204 can have an outer diameter that is at least about 2 times larger than the internal diameter, 3 times larger, or 4 times larger. In the same or alternative embodiments, the capillary tube can have an internal diameter that is less than about 75%, about 50%, about 30%, about 20% about 10%, about 5%, or 1% of the outer diameter of the capillary tube 704.

In various embodiments, the smaller inner NMR tube 202 can be about 203 mm in length and about an 0.8 mm internal diameter. In the same or alternative embodiments, the NMR tube 202 can be about 178 mm in length and about a 4.2 mm internal diameter.

As discussed below, in certain embodiments, it may be beneficial to seal the capillary tube 204 so that the reference sample is sealed off from the target sample in the NMR tube 202.

As seen in FIG. 2, the temperature sensor device 200 only includes one reference capillary tube 204, and in this embodiment the capillary tube 204 is centrally located. In alternative embodiments, when more than one reference capillary tube is utilized in the NMR tube 202, these capillary tubes may be spatially arranged, e.g., to measure temperature gradients that may span the target sample.

In various embodiments, a temperature sensor device for use with a solid sample is disclosed. In such embodiments, an external in situ capillary NMR thermometer device for a solid sample can include a capillary tube of a desired length with the reference material (such as ethylene glycol) centrally embedded in the sample contained in a Magic Angle Spinning (MAS) rotor. Such a device is described further below with respect to FIG. 3.

In one or more embodiments, an external in situ capillary NMR thermometer device for a solid sample may include multiple capillary tubes of a desired length with the reference material. In such embodiments, the capillary tubes may be spatially disposed within the sample to monitor spatial variations in sample characteristics, such as the variation of temperature at various locations in the sample contained in the cylindrical rotor.

Figure 3:
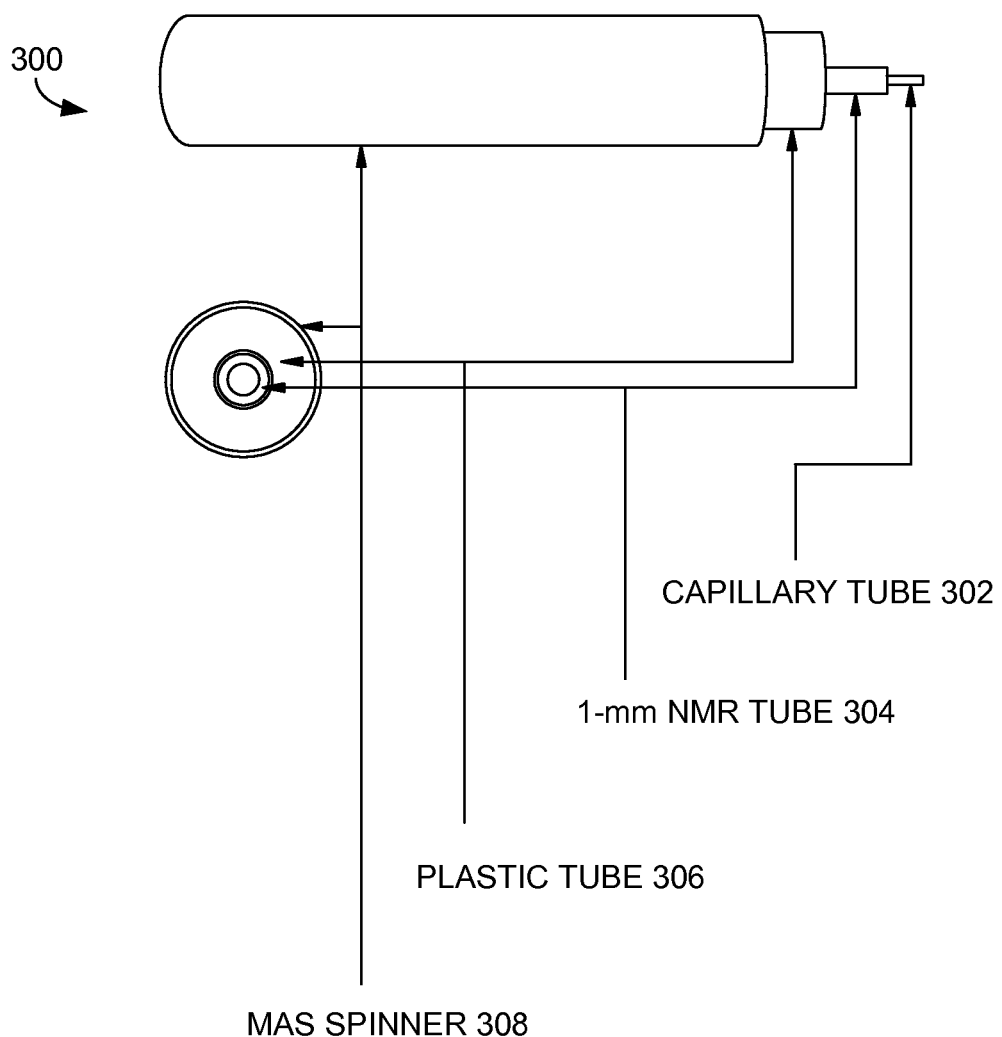
FIG. 3 depicts another in situ NMR thermometer, according to one embodiment described herein.

FIG. 3 depicts a temperature sensor device 300 for in situ temperature measuring for solid state NMR. As shown in FIG. 3, the temperature sensor device 300 can include a sealed capillary tube 302 with a reference material centrally placed in the sample (e.g., a pressed powder) contained in the Magic Angle Spinning (MAS) rotor 308. In the embodiment depicted in FIG. 3, the capillary tube 302 is positioned inside of a 1 mm NMR tube 304, which is positioned inside of a plastic tube 306, which is positioned inside of the MAS rotor. In embodiments, the 1 mm NMR tube 304 and the plastic tube 306 are used to center with capillary tube 302 when no target sample or a minimal amount of target sample used in the MAS rotor.

In embodiments, that do not require a NMR tube 304 and/or a plastic tube 306, the temperature sensor device 300 may only include the MAS rotor 308 and the capillary tube 302. In such embodiments, a powder sample can be packed inside the MAS rotor 308. Further, in such embodiments, a drill bit or similar device can be used to bore a hole in the sample centrally located in the MAS rotor 308. In addition, in such embodiments, a sealed capillary tube 302 with reference material is placed in the bored hole. Further, a packing tool having an end in the shape of a tube is used to pack the powder sample tightly around the sealed capillary tube 302.

As discussed above, a capillary tube, e.g., the capillary tube 204 and/or the capillary tube 302, can include a reference material for the in situ measurement of pH. The reference material may be one or more of compounds that have one or more NMR peaks that change chemical shift as a function of temperature. The reference material may be a liquid, solid, and/or gaseous material. In one or more embodiments, a liquid reference material may include one or more of ethylene glycol, methanol, ethanol, NaF in $D_2O$, alcohols, glycols, polyethylene glycols. In various embodiments, solid reference materials may include one or more of lead nitrate, cobalt complexes, etc. In certain embodiments, gaseous reference materials include one or more of methane, xenon, mixture of xenon with oxygen, $CF_4$, $CF_2(OF)_2$, $CF_3C_{F3}$, $CF_2CF_2$.

The capillary tubes 204 and 302, may in various embodiments, may include one or more materials that include glass, quartz, Peek, Torlon, Teflon, Arum, and other polymers and ceramic materials. In one embodiment, the capillary tubes 204 and 302 do not include a metal material.

Systems and Methods for Sealing a Capillary Tube for an in situ NMR Thermometer

As discussed above, one or more capillary tubes that house the temperature reference material for an in situ NMR thermometer may be sealed. It is appreciated that the sealing system and methods described herein can be useful for use with other devices, in addition to an in situ NMR thermometer, such as devices requiring sealed capillaries to survive at high temperatures and pressures in harsh environments.

In embodiments, a glass seal may be used at one or both ends of the capillary tube. In certain embodiments, an Optical Fiber Arc Fusion Splicer may be used to generate such a glass seal.

In certain embodiments, a method generally comprises the steps of i) selecting a suitable capillary tube with desired length, internal diameter, and outer diameter for a particular application, ii) filling said capillary tube with preselected (solid, liquid, or gas) reference material, iii) sealing a first end of such capillary tube, and iv) sealing a second end of capillary tube, whereas sealing a capillary tube may involve means of glue, epoxy, plugs, etc., or an electric arc fusion approach utilizing an Optical Fiber Arc Fusion Splicer.

According to an exemplary embodiment of the invention, the inventive method for sealing a capillary tube comprises the following steps:

(1) Use epoxy to seal a needle to one end of a desired capillary tube.
(2) Use a knife to scrape off the coating (about 1 cm long) from the other end of the capillary tube.
(3) Fill a sample solution into a syringe.
(4) Connect the needle to the syringe.
(5) Push the solution though the capillary tube until 2 to 3 drops comes out of the open end of the capillary tube.
(6) Wipe the end of the capillary tube.
(7) Place the open end of the capillary tube in the arc fusion splicer.
(8) Check the fusion splicer display screen to find the gas/liquid interface.
(9) Push the syringe plunger in order to keep the gas liquid interface about 0.1 mm from the open end of capillary tube.
(10) Apply the arc with a constant 0.05N force on the syringe plunger.
(11) Take the sealed capillary tube out of the arc fusion splicer.
(12) Choose the length of the capillary tube that you want, and cut off the portion that is affixed to the syringe needle.
(13) Use a knife to scrape off the coating (about 1 cm long) from the open end of the capillary tube.
(14) Place the open end of the capillary tube in the arc fusion splicer, and then apply the arc.
(15) Use a microscope to check the sealed ends of the capillary tube.

Figure 4:
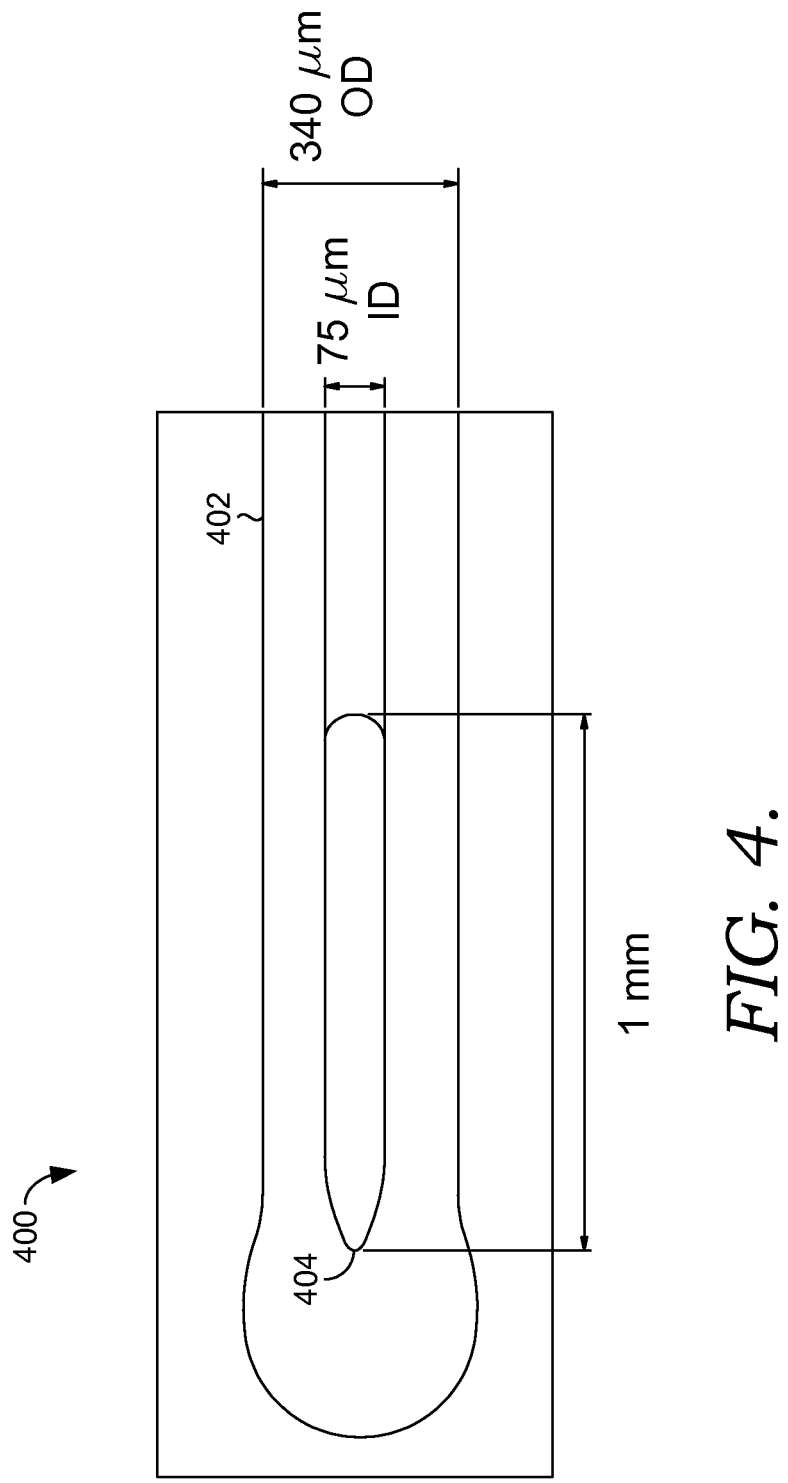
FIG. 4 depicts a schematic view of a sealed capillary tube end, according to one embodiment described herein.

A schematic representation 400 of a sealed capillary tube 402 is depicted in FIG. 4. The capillary tube 402 includes an end 404 that is sealed by glass or other material from the capillary tube 402. In embodiments, when using an Optical Fiber Arc Fusion Splicer to seal the end 404 of a capillary tube 402, it may be beneficial to maintain a liquid, gas, or solid reference material inside the capillary tube 402 at least about 1 mm away from the end 404 of the tube so as to not inadvertently heat up the reference material. In various embodiments, the reference material should be kept at least about 0.75 mm away from the end 404 being sealed by the Optical Fiber Arc Fusion Splicer, or at least about 0.5 mm, or at least about 0.3 mm, or at least about 0.1 mm.

Solid State In Situ Measuring Devices and Methods for Quantifying One or More Properties of a Target Sample As discussed above, embodiments disclosed herein concern in situ measuring devices, methods of making in situ measuring devices, and methods for utilizing in situ measuring devices in solid-state NMR for the quantitative determination of various properties of a target sample, such as chemical shifts, amounts of a target sample material, and temperature of the target sample material in an unknown sample. Generally, in embodiments, an in situ measuring device can include one or more reference materials sealed in a capillary tube, where the sealed capillary tube is positioned inside of a solid state NMR MAS rotor amongst a target sample. In such embodiments, the in situ measuring devices described herein can provide a single device having a reference material for calibration or other reference measurements that is physically separated from a target sample, where both the reference material and the target sample are in one single solid state NMR MAS rotor.

The in situ measuring devices described herein, e.g., the in situ measuring devices described below with reference to FIGS. 13A. 13B, and 14A, can allow for the simultaneous, or near simultaneous recording of NMR spectra of the reference sample and of the target sample material in the MAS or solid state NMR rotor. This simultaneous or near simultaneous recording of NMR spectra of both a calibration or reference material and a target sample creates a single set of NMR spectra imprinted with calibration or reference material spectral data. That is, utilizing the in situ measuring devices disclosed herein, such as the in situ measuring devices 1300 and 1400 discussed below, one can obtain NMR spectra of the target sample material that also includes the NMR spectra of the reference or calibration material. Such target sample data imprinted with the calibration or reference data is critical in solid state NMR measurements, as the NMR spectra of the calibration or reference material is collected in the same or substantially the same environment and at the same time as the NMR spectra of the target sample material.

This simultaneous or near simultaneous recording of the NMR spectra of the reference material and the target sample material avoids problems associated with the conventional solid state NMR calibration techniques, which can include the sequential measurement of a reference material and a target sample. For example, in such a conventional technique, when one is calibrating the NMR spectra of a target sample using a reference material NMR spectra, one relies on the assumption that the environment of the reference sample in the NMR instrument when the reference NMR spectra are obtained is identical to the environment of the target sample when the target sample NMR spectra are obtained, even though such NMR spectra were obtained at different times. The in situ measuring devices described herein allow one to eliminate such an assumption since the reference sample and target sample are both in the NMR probe at the same time, thereby allowing for simultaneous or near simultaneous recording of NMR spectra.

In certain embodiments, such an in situ measuring device can include a sealed capillary tube having a reference material inside the capillary tube, and the sealed capillary tube can be positioned inside of a MAS or solid state NMR rotor. In such embodiments, the sealed capillary tube may be positioned within a target sample of interest that is inside the MAS rotor. In one or more embodiments, an in situ measuring device can include a plurality of sealed capillary tubes, each potentially containing a reference material therein, where the plurality of sealed glass capillary tubes are centrally or spatially arranged in a rotor, e.g., among a solid sample.

Figures 13A, 13B:
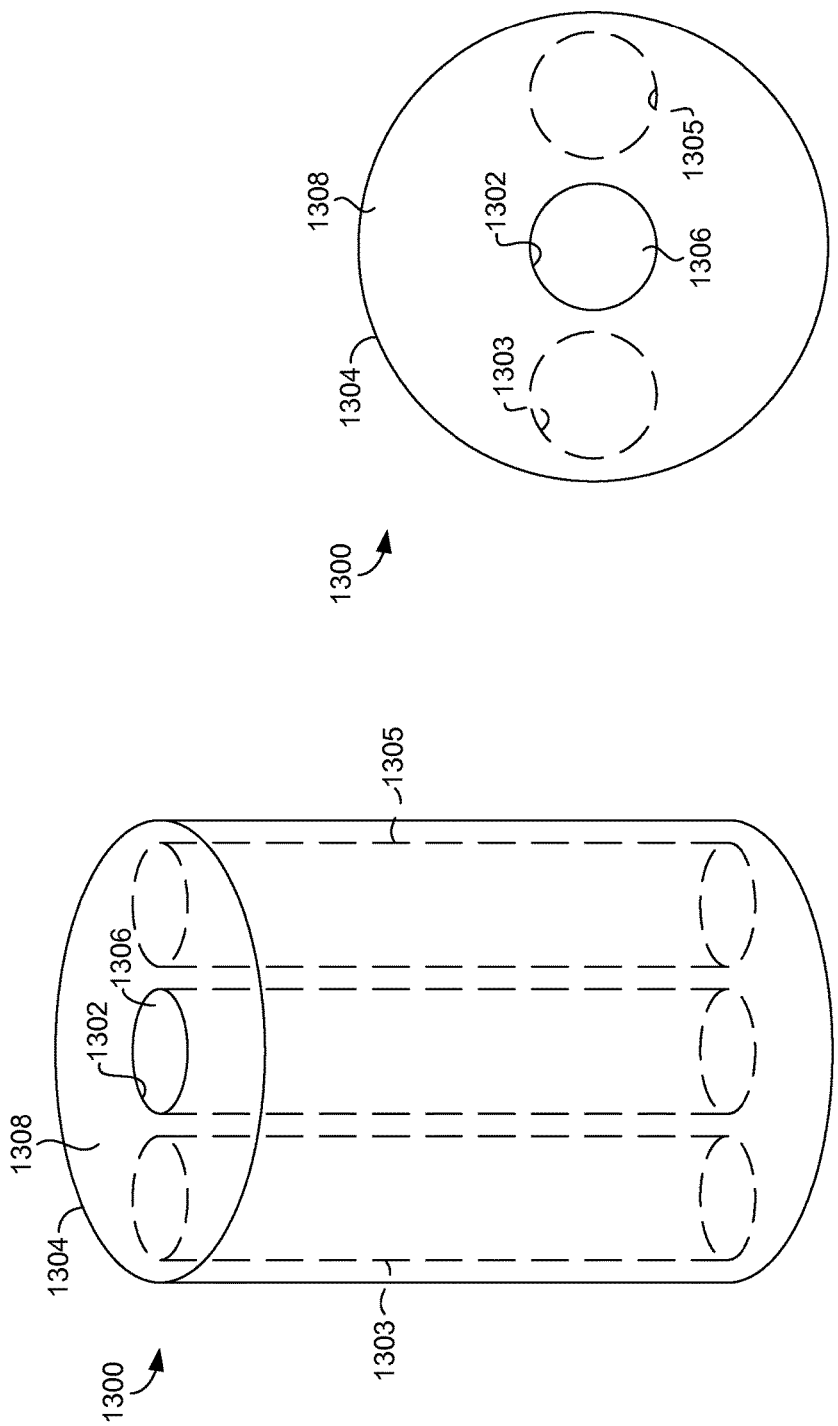
FIG. 13A depicts a schematic side perspective view of an in situ measuring device, particularly showing a capillary tube positioned inside of a solid state NMR or MAS rotor, according to one embodiment described herein.
FIG. 13B depicts a top view of the in situ measuring device of FIG. 13A, according to one embodiment described herein.

An embodiment of the in situ measuring device 1300 is depicted in FIGS. 13A and 13B. The in situ measuring device 1300 can include a capillary tube 1302 positioned inside of a MAS rotor 1304. In certain embodiments, a plurality of capillary tubes can be present in the in situ measuring device. For example, as depicted in FIGS. 13A and 13B, in addition to the capillary tube 1302, capillary tubes 1303 and 1305 (shown in phantom lines) may also be present. While only three capillary tubes are depicted, it is appreciated that any number of capillary tubes may be utilized in the in situ measuring devices described herein. It is also appreciated that one skilled in the art would understand that when using a plurality of capillary tubes in the in situ measuring device 1300, it can be beneficial to arrange them such that the in situ measuring device is balanced for spinning in an NMR instrument. While, herein, properties and processes are described primarily with respect to the capillary tube 1302, it should be understood that such descriptions equally apply to all or any of the plurality of capillary tubes in the in situ measuring device 1300 (or in the in situ measuring device 1400 discussed below with reference to FIG. 14A).

In embodiments, the sealed capillary tube 1302 can be made from any type of common material used to make capillary tubes, as long as such material is capable of withstanding the forces in the spinning MAS rotor in an MAS-NMR experiment. In one or more embodiments, the sealed capillary tube 1302 can be made from borosilicate glass and/or one or more polymeric materials, such as polyether ether ketone.

In certain embodiments, the sealed capillary tube 1302 can be any size that is capable of fitting inside of a conventional, commercially available MAS rotor. In certain embodiments, the sealed capillary tube 1302 can have a length of at least about 10 millimeters, or at least about 20 millimeters, or at least about 40 millimeters, or at least about 50 millimeters. In embodiments, the sealed capillary tube 1302 can have an internal diameter of at least about 50 micrometers, or at least about 100 micrometers, or at least about 200 micrometers, or at least about 500 micrometers, or at least about 1 millimeter, or at least about 1.2 millimeters; and/or an outer diameter of at least about 250 micrometers, or at least about 350 micrometers, or at least about 500 micrometers, or at least about 700 micrometers, or at least about 1 millimeter, or at least about 1.4 millimeters. In certain embodiments, the sealed capillary tube 1302 can have an internal diameter of about 150 micrometers, an outer diameter of about 365 micrometers, and a length of about 13 millimeter. In alternative embodiments, the sealed capillary tube 1302 can have an internal diameter of about 1.2 millimeters, an outer diameter of about 1.4 millimeters, and a length of about 13 millimeters.

As discussed above, the sealed capillary tube 1302 can include a reference material positioned in the interior 1306 of the sealed capillary tube 1302. The reference material can be any material that could be used for calibration and/or as a reference for NMR measurements, such as solid state NMR measurements. In various embodiments, the reference material can be one or more compounds that have one or more sharp NMR peaks spaced apart from the NMR peaks of the target sample. In one or more embodiments, the reference material can include ethylene glycol, ethanol, methanol, water, and/or mixtures thereof.

In one or more embodiments, the reference material can be inserted into the interior 1306 of the capillary tube 1302 using any technique known to one skilled in the art. An exemplary method for adding a reference material into the interior 1306 of the capillary tube 1302 can include the use of a syringe needle. For example, in such embodiments, the capillary tube 1302 can be inserted into the needle of a syringe and sealed at the end of the needle with epoxy glue or any other appropriate glue that creates an air-tight seal and bond between the capillary tube 1302 and the needle. Further, in such embodiments, the syringe (filled with the reference material) can be used to fill the capillary tube 1302 by the application of moderate pressure put on the syringe's piston until the capillary tube 1302 is completely filled with the reference material. In addition, in such embodiments, it may be beneficial to visually inspect, e.g., under a lens or optical microscope, to ensure that no air bubbles remain inside the capillary tube 1302.

In embodiments, the capillary tube 1302 can be sealed using any technique that is capable of sealing one or more ends of the capillary tube 1302. In one or more embodiments it may be advantageous to seal the capillary tube 1302 in such a manner that the capillary tube 1302, or the in situ measuring device 1300, would not be unbalanced for spinning in an MAS or solid state NMR experiment. In certain embodiments, the capillary tube 1302 can be sealed with Teflon® tape. In alternative embodiments, the capillary tube 1302 may be sealed by the arc of a glass fiber fusion splicer (OPTICAL FIBER FUSION SPLICER, MODEL: TYPE-36) or any other appropriate fusion splicer. In embodiments, where the capillary tube 1302 was filled with the reference material via a syringe such that one end of the capillary tube 1302 is bonded to the syringe, as discussed above, the open end of the capillary tube 1302 opposite to the end bonded to the syringe needle may be the end that is sealed first. Then, the end of the capillary tube 1302 bonded to the syringe needle is cut to a desired length and also sealed by a desired method.

In one or more embodiments, the capillary tube 1302 can be flame sealed, e.g., via the use of a commercially available micro torch. In certain embodiments, an exemplary method for sealing the capillary tube 1302 using a micro torch can include concentrically mounting the capillary tube 1302 at the top of the spindle of a commercially available stepper motor. In such embodiments, a thin metal plate can be prepared with a hole 1.6 millimeter in diameter and can be positioned above a conventional stepper motor such that the capillary reference tube passes through the hole in the metal plate and extends above the metal plate by about 1 millimeter.

Further, in such embodiments, the stepper motor can be activated, thereby causing the capillary tube 1302 to rotate at about 2-4 revolutions per second. The flame of the micro torch, burning a combustible gas, may be aimed at the 1 millimeter portion of the glass reference capillary tube that extends above the metal plate. In embodiments, the metal plate is utilized to prevent the flame and heat from impacting the portion of the reference capillary tube 1302 that may contain the reference material, which may be positioned below the metal plate. Further, a stream of very cold nitrogen gas may be directed at the portion of the glass capillary reference sample tube that is located below the metal plate for the purpose of cooling the capillary tube 1302 and the reference material. The purpose of cooling the reference material is to prevent evaporation and degradation caused by the high temperatures from this glass-sealing process. Cooling of the capillary tube 1302 can be performed to maintain the reference material at temperatures above, below or at room temperature. It may be advantageous to maintain the temperature of the reference material below its freezing point so that very little volatility occurs. The cooling gas may be applied to the bottom of the capillary tube 1302 after the flame is applied to the top of the tube. Using this sequence, the mixture of reference sample vapor and air (located above the liquid reference sample), which may contain water vapor and other gaseous impurities, may be caused to be excluded from the capillary tube 1302 before it was completely sealed. Continuous or intermittent applications of the flame to the top, open portion of the capillary tube 1302, which may be rotated by the stepper motor, can cause the glass or other material of which the capillary tube 1302 is comprised to melt and close the tube opening. At the moment that the seal is fully formed, the flame may be turned away from the capillary tube 1302. The soft molten glass or other material may form a small expanded bubble that may be approximately 2 millimeters in diameter, which may be treated by cooling to room temperature and applying intermittent heat for purposes of annealing such a glass bubble.

As discussed above, the in situ measuring device 1300 can include one or more sealed capillary tubes, e.g., the sealed capillary tube 1302, positioned in the interior 1308 of the MAS or solid state rotor 1304. One exemplary method for positioning the sealed capillary tube 1302 in the interior 1308 of the MAS rotor can include first completely filling an open end of the MAS rotor 1304 with a solid substance under investigation (e.g., the target sample of interest), which could be crystalline, amorphous, gel-like or in any state that stays in its shape even after machining with tools. In such embodiments, the target sample can be compacted to a desired density, as done by one skilled in the art in conventional solid-state NMR experimentation. Further, in such embodiments, a small hole of a diameter that matches the outside diameter of the capillary tube 1302 can be drilled precisely along the long axis of the MAS rotor 1304 into the compacted target sample material, which can allow the sealed capillary tube 1302 to be inserted snuggly into this drilled hole. In alternative embodiments, this hole may be fabricated by other hole-generating tools and/or the hole could have been aligned parallel to the long axis of the MAS rotor but off its center. In addition, in such embodiments, the sealed capillary tube 1302 can be inserted into the prepared hole in the target sample material, and the target sample material around the capillary tube 1302 may be compacted again, as needed. Finally, in such embodiments, the MAS rotor 1304 can be closed and/or sealed with the standard rotor lid and prepared to be inserted into the solid-state NMR probe for the recording of NMR spectra.

Figure 14B:
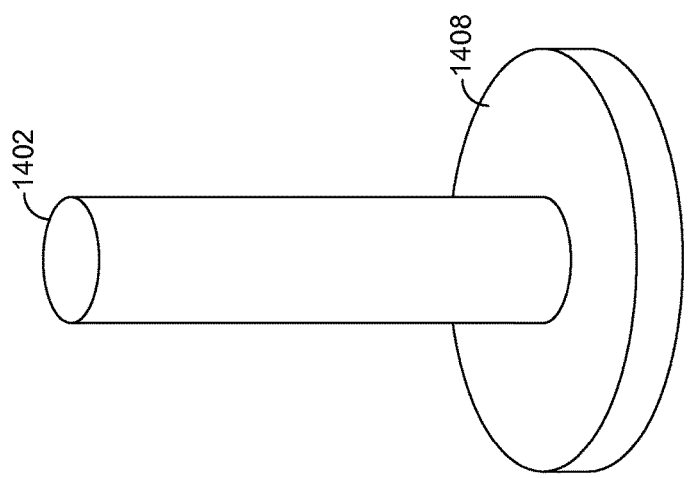
FIG. 14B depicts the capillary tube and foundation member of the in situ measuring device of FIG. 14A positioned outside of the solid state NMR or MAS rotor, according to one embodiment described herein.
Figure 14A:
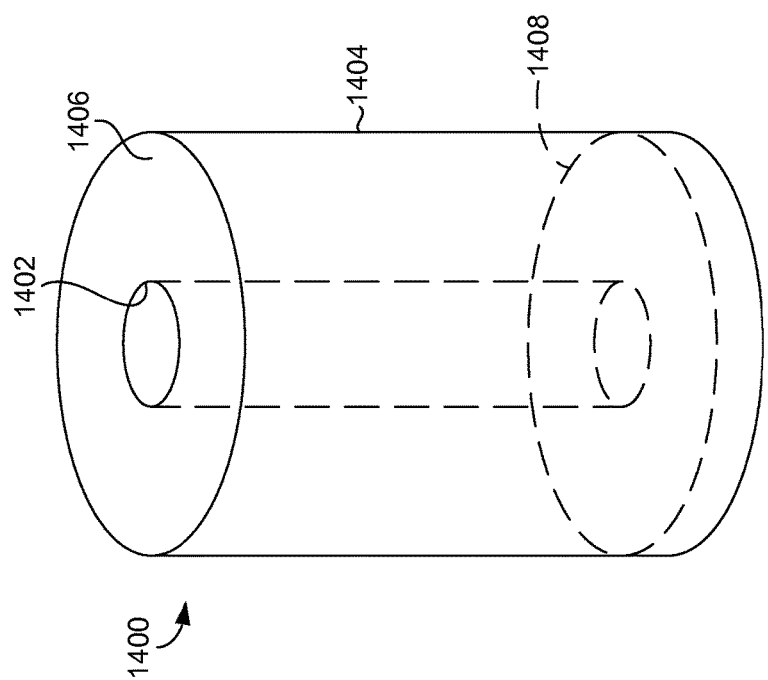
FIG. 14A depicts a schematic side perspective view of an in situ measuring device, particularly showing a capillary tube coupled to a foundation member, where the capillary tube and foundation member are positioned inside of a solid state NMR or MAS rotor, according to one embodiment described herein.

FIG. 14A depicts another embodiment of an in situ measuring device 1400. The in situ measuring device 1400 includes a sealed capillary tube 1402 positioned in the interior 1406 of MAS rotor 1404. The in situ measuring device 1400 depicted in FIG. 14A also includes a foundation 1408 fused to the sealed capillary tube 1402. In embodiments, the foundation 1408 fused to the sealed capillary tube 1402 allows for an alternative method for forming an in situ measuring device, e.g., the in situ measuring device 1400, compared to method of forming the in situ measuring device 1300 discussed above with reference to FIG. 13. That is, by having a foundation 1408 fused to the sealed capillary tube 1402 (as depicted in FIG. 14B, the capillary tube may be inserted into the MAS rotor 1404 prior to adding the target sample material, as opposed to adding the capillary tube 1302 to target sample-filled MAS rotor 1300, as discussed above with reference to FIG. 13.

In embodiments, one method for forming the in situ measuring device 1400 of FIG. 14A can include fusing, flame-sealing, or gluing the capillary tube 1402 to the foundation 1408 such that the sealed capillary tube 1402 is perpendicular to the foundation 1408, as depicted in FIG. 14B. The sealed glass capillary tube can be placed in the center or at any other location on the foundation 1408. The foundation 1408 can be comprised of a glass, ceramic, and/or a polymeric material. The sealed capillary tube 1402 can be coupled to the outer surface of the foundation 1408 or can be coupled to a hole in the foundation 1408 designed to fit the sealed capillary tube 1402. In embodiments, once the sealed capillary tube 1402 is coupled to the foundation 1408, it can be inserted into an NMR solid-state sample rotor, e.g., the MAS rotor 1404. In embodiments, after the capillary tube 1402—foundation 1408 assembly is placed in the MAS rotor 1404, the MAS rotor 1404 can be filled with the target sample of interest, and can be compacted, as needed. Further, a MAS rotor lid can then be placed on the top of the MAS rotor 1404 to seal the MAS rotor 1404, and the in situ measuring device 1400 can be inserted into the NMR probe for recording NMR spectra.

The in situ measuring devices 1300 and 1400 discussed above with reference to FIGS. 13A, 13B, and 14A, allow for the simultaneous recording of NMR spectra of the reference sample inside the capillary tube, e.g., the capillary tubes 1302 and/or 1402, and of the target sample material in the MAS rotor. This simultaneous recording of NMR spectra of a calibration or reference material and a target sample creates a single set of NMR spectra imprinted with calibration or reference material data. That is, utilizing the in situ measuring devices disclosed herein, such as the in situ measuring devices 1300 and 1400 discussed above with reference to FIGS. 13A, 13B, and 14A, can provide NMR spectra of the target sample material that also includes the NMR spectra of the reference or calibration material. Such imprinted calibration or reference data is critical in solid state NMR measurements, as the NMR spectra of the calibration or reference material is collected in the same exact environment and same time as the NMR spectra of the target sample material.

As discussed above, in certain embodiments, the in situ measuring devices disclosed herein, such as the in situ measuring devices 1300 and 1400 discussed above with reference to FIGS. 13A, 13B, and 14A, can be utilized to determine the quantity, identity, and/or the temperature of a target sample material in an unknown, or known, sample. For example, in one or more embodiments, one can determine the number of protons in a target sample material of an unknown sample, by adding a measured amount (e.g., weighed amount) of a known reference material inside a capillary tube, e.g., the capillary tube 1302 of the in situ measuring device 1300 discussed above with reference to FIG. 13A and FIG. 13B. In such embodiments, one can then add an unknown material to the MAS rotor, e.g., the MAS rotor 1304 of the in situ measuring device 1300 discussed above with reference to FIG. 13A and FIG. 13B and record proton NMR spectra. In one or more embodiments, one can record the proton solid state NMR spectra using the Bloch Decay Pulse Sequence experiment and then perform a Fourier Transform of the proton MAS spectra using commercial NMR software. In such embodiments, the spectra can be analyzed using standard baseline correction and integration procedures. In such embodiments, one can then identify a particular proton peak, e.g., the $CH_2$ peak of ethylene glycol, in the NMR spectra of the reference material using known methods, and integrate such a peak using known methods, to obtain a ratio of and compare by ratio to the integration of the proton peaks of the unknown material to obtain the number of protons in the unknown sample. Example 6 below, describes an embodiment of this process further detail.

In certain embodiments, one can determine the chemical identity of a target sample material of an unknown sample, by utilizing the in situ measuring devices described herein. For example, one may utilize a known reference material inside a capillary tube, e.g., the capillary tube 1302 of the in situ measuring device 1300 discussed above with reference to FIG. 13A and FIG. 13B to obtain a Carbon Bloch Decay Magic Angle Spinning NMR spectrum of the reference material and of the unknown. In such embodiments, one can then calibrate the chemical shift axis of this spectrum using a particular carbon in the known reference material (e.g., the methylene carbon peak of ethylene glycol), and then one can identify the chemical shifts of carbon peaks of the unknown sample and then compare those to the chemical shifts of carbon peaks known in the field, to obtain information on all types of chemical carbons in the unknown sample. Example 7 below describes an embodiment of this process further detail.

In one or more embodiments, one can determine the temperature of a target sample material of an unknown sample, by utilizing the in situ measuring devices described herein. For example, one may utilize a known reference material inside a capillary tube, e.g., the capillary tube 1302 of the in situ measuring device 1300 discussed above with reference to FIG. 13 to obtain proton Magic Angle Spinning NMR spectra of the reference material and the unknown sample. In such embodiments, the reference sample may reveals at least two peaks for particular types of protons, e.g., the $CH_2$ and OH groups of ethylene glycol. Further in such embodiments, the difference between the resonance frequencies of these two peaks can be used as a numerical input to calculate the absolute temperature of the unknown sample using a conventional equation known to one skilled in the art (e.g., *J. Magn. Reson.* 1982, 46, 319-321, which is incorporated by reference herein). It is well known in the art that the chemical shifts and widths for peaks in the proton NMR spectra of materials change as a function of temperature and in doing so reveal the specific molecular dynamics that the materials undergo. Molecular dynamics information may be useful for characterizing the dynamic architecture of materials and is used to explain the physical properties (e.g., glass transition temperature) of various materials, including polymeric materials.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

EXAMPLES

The concepts discussed herein will be further described in the following examples, which do not limit the scope of various embodiments described in the claims.

Example 1: Phenolphthalein as a pH Sensor for In Situ pH Measurements

In this example, the in situ pH measuring device included a standard NMR tube as the sample housing member where a sample (in the sample solution) was contained and a central capillary tube made of VYCOR® glass as the containment member was used where the pH sensor was contained. In this example, phenolphthalein was utilized as the pH sensor.

Specifically, the exemplary embodiment comprised a commercial 5 mm outer diameter, 17 cm long borosilicate glass NMR tube as the sample housing member and a 1 mm outer diameter, 17 cm long VYCOR® porous capillary tube as the containment member for the pH sensor molecule phenolphthalein. The size of a sequestered phenolphthalein molecule is approximately seven Angstroms; the VYCOR® porous capillary pH sensor tube is selected for pore sizes that are smaller than the phenolphthalein molecule, but large enough (about two Angstroms in diameter) to allow unobstructed passage of hydronium and hydroxide ions. During the NMR testing, the VYCOR® porous capillary tube was filled to a height of approximately 7 cm from the bottom with a 0.001 molar aqueous solution of phenolphthalein, and placed approximately concentrically within the 5 mm glass NMR tube. The target sample, an aqueous acid solution, analyzed by NMR or MRI methods was placed inside the annular volume between the outside wall of the containment tube and the inside wall of the 5 mm glass NMR tube and filled to a level of approximately 7 cm from the bottom of both tubes. Standard NMR and MRI analyses were performed on the entire concentric tube assembly. The resulting proton NMR signals that emanated from the target sample solution and the phenolphthalein pH sensor molecule were recorded simultaneously and synchronously by the NMR spectrometer and were inextricably comingled in the raw data structure, also known as the free induction decay (FID). A fast Fourier transform (FFT) was applied to the FID data to generate a proton NMR spectrum of the target sample solution and the phenolphthalein pH sensor molecule.

To generate the NMR spectra, 3 microliters of a 0.01 molar NaOH solution was added to the NMR tube and the proton NMR spectrum was recorded. This was repeated (ten times) until a total of 30 microliters had been added. Additionally, an electronic pH meter was utilized to test the pH of each different target sample solution that was in the NMR tube.

Figure 5A:
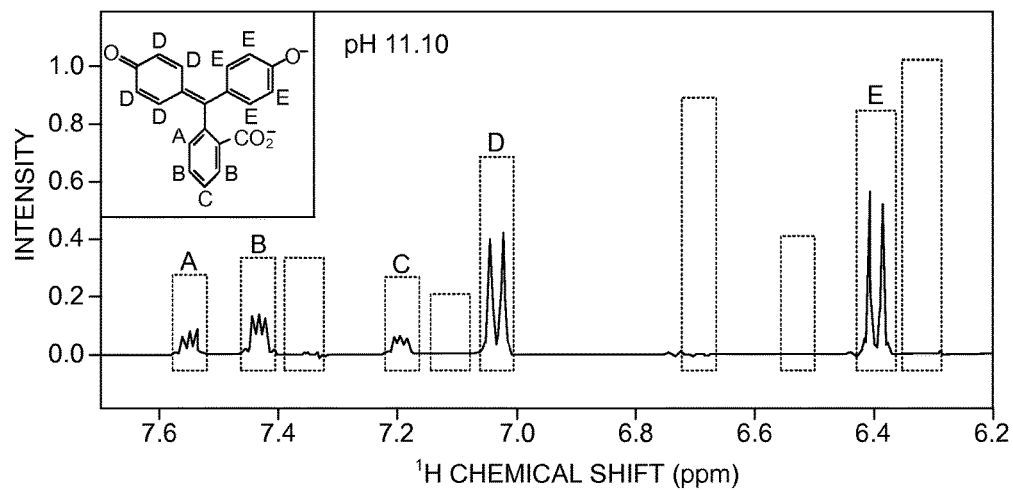
FIG. 5A is a graph of proton NMR peaks of phenolphthalein at a pH of 11.1 as described in Example 1, according to one embodiment described herein.
Figure 5B:
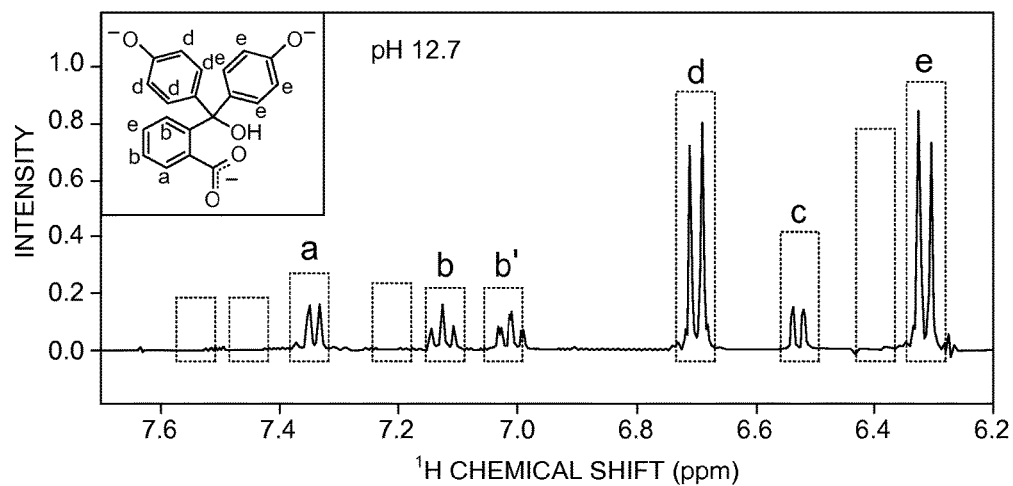
FIG. 5B is a graph of proton NMR peaks of phenolphthalein at a pH of 12.7 as described in Example 1, according to one embodiment described herein.

The phenolphthalein molecule is known to exist exists in two different structural forms depending on the pH of the solution. FIGS. 5A and 5B illustrate the pH induced spectral changes of the exemplary pH sensor (phenolphthalein) at two different pH values. One form of the pH sensor probe molecule is shown in FIG. 5A for pH 11.1; a different structural form of the pH sensor probe molecule is shown in FIG. 5B for pH 12.7.

A comparison of FIG. 5A and FIG. 5B reveals two sets of proton NMR peaks for the pH sensor probe molecule phenolphthalein when it exists in two different forms, under conditions of different pH. The proton resonances for each group of chemically equivalent protons are contained in eleven distinct boxes and labeled with capital letters (FIG. 5A) or lower case letters (FIG. 5B) according to each of the respective structures depicted in FIGS. 5A and 5B. At pH 11.1 only one form of phenolphthalein molecule is present, while at pH 12.7 only the other form is present. These changes in peak intensities of the 1H NMR spectrum of the phenolphthalein pH sensor were correlated with the electronically-measured pH values that ranged from pH 11.1 to 12.7.

Figure 5C:
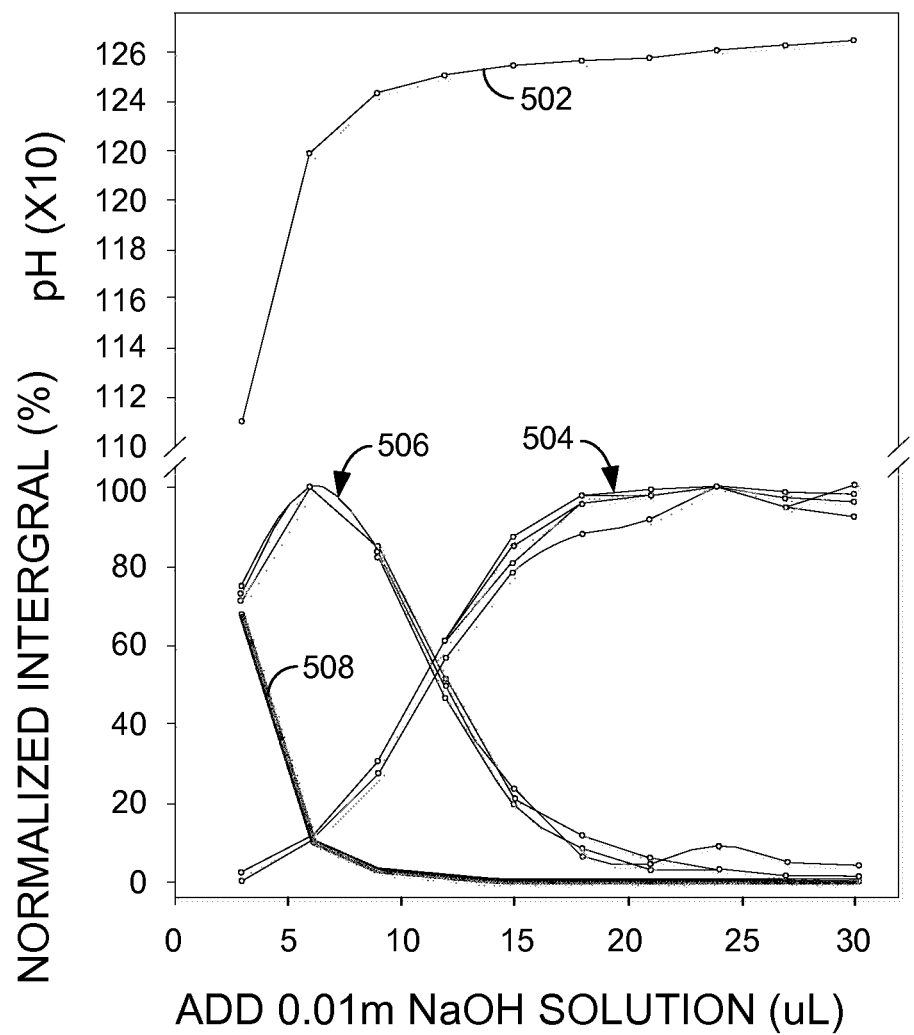
FIG. 5C is a graph containing multiple plots of peak integrals, ratios of peak integrals and pH values for a phenolphthalein solution as described in Example 1, according to one embodiment described herein.

Measurements of the intensities from both sets of proton NMR peaks from FIGS. 5A and 5B are plotted in FIG. 5C, and were used in conjunction with a pH calibration curve shown in the top portion of FIG. 5C to determine the pH of the target sample solution. FIG. 5C is a graph containing multiple plots of peak integrals and pH values for a solution of 7.7 mg of phenolphthalein in 600 microliters of $D_2O$ as a function of 3 microliter additions of 0.01 molar NaOH. The group of lines 506 are plots of normalized proton NMR peak integrals for the phenolphthalein structure shown in FIG. 5A as a function of 3 microliter additions of 0.01 molar NaOH. The group of lines 504 are plots of normalized proton NMR peak integrals for the phenolphthalein structure shown in FIG. 5B as a function of 3 microliter additions of 0.01 molar NaOH. The line 508 is a plot of the ratio of intensities of corresponding selected peaks from the proton NMR spectra from FIGS. 5A and 5B. The line 502 is a plot of the measured pH using an electronic pH meter. The proton NMR spectra for phenolphthalein solutions at pH values between 11.1 and 12.7 revealed the proton resonances for both structures in varying proportions.

The absolute intensity of each peak in the spectrum was measured by integration over the signal. Further, a mathematical correlation function was used to calculate the pH from a 1H NMR peak intensity of phenolphthalein pH sensor molecule. The pH was corrected for temperature variation by repeating the previous steps for each temperature setting for a series of temperatures that covered the temperature range of interest for investigations of the target sample solution. This example provides the paradigm for in situ monitoring of pH by $^1$H NMR spectroscopy via peak intensities with the advantage of a spectral pH imprimatur.

Example 2: NaF as a pH Sensor for In Situ pH Measurements

In this example, the pH-induced spectral changes of another exemplary pH sensor, sodium fluoride (NaF), was categorized by Fluorine-19 NMR chemical shift. The in situ pH measuring device utilized in this example includes a commercial 5 mm outer diameter, 17 cm long borosilicate glass NMR tube as the sample housing member and a 1 mm outer diameter, 17 cm-long cracked-tip capillary pH sensor tube as the containment member for the pH sensor molecule, NaF. The cracked-tip capillary tube was prepared by heating the bottom (closed end) of the tube and rapidly quenching the hot glass in cold water, causing a crack in the glass. The size of a sequestered solvated NaF molecule is approximately three Angstroms, and thus, the cracked-tip capillary pH sensor tube was selected for crack sizes that are smaller than the solvated NaF molecule, but large enough (about two Angstroms in diameter) to allow unobstructed passage of hydronium and hydroxide ions. The cracked-tip capillary tube was filled to a height of approximately 7 cm from the bottom with a 0.001 molar aqueous solution of NaF, and placed approximately concentrically within the 5 mm glass NMR tube.

The target sample material analyte molecule (1,1,1,2,2-pentafluorododecan-3-ol) was analyzed by NMR or MRI methods by placing an aqueous solution of it inside the annular volume between the outside wall of the cracked-tip pH sensor tube and the inside wall of the 5 mm glass NMR tube, filled to a level of approximately 7 cm from the bottom of both tubes. Standard 19F NMR and MRI analyses were performed on the concentric tube assembly. The resulting fluorine-19 NMR signals that emanated from the sample material (1,1,1,2,2-pentafluorododecan-3-ol) and the NaF pH sensor probe molecule were recorded simultaneously and synchronously by the NMR spectrometer and were inextricably comingled in the raw data, also known as the free induction decay (FID). A fast Fourier transform (FFT) was applied to the FID to generate an 19F NMR spectrum of the target sample material analyte molecule (1,1,1,2,2-pentafluorododecan-3-ol) and the sodium fluoride pH sensor probe molecule.

Figure 6:
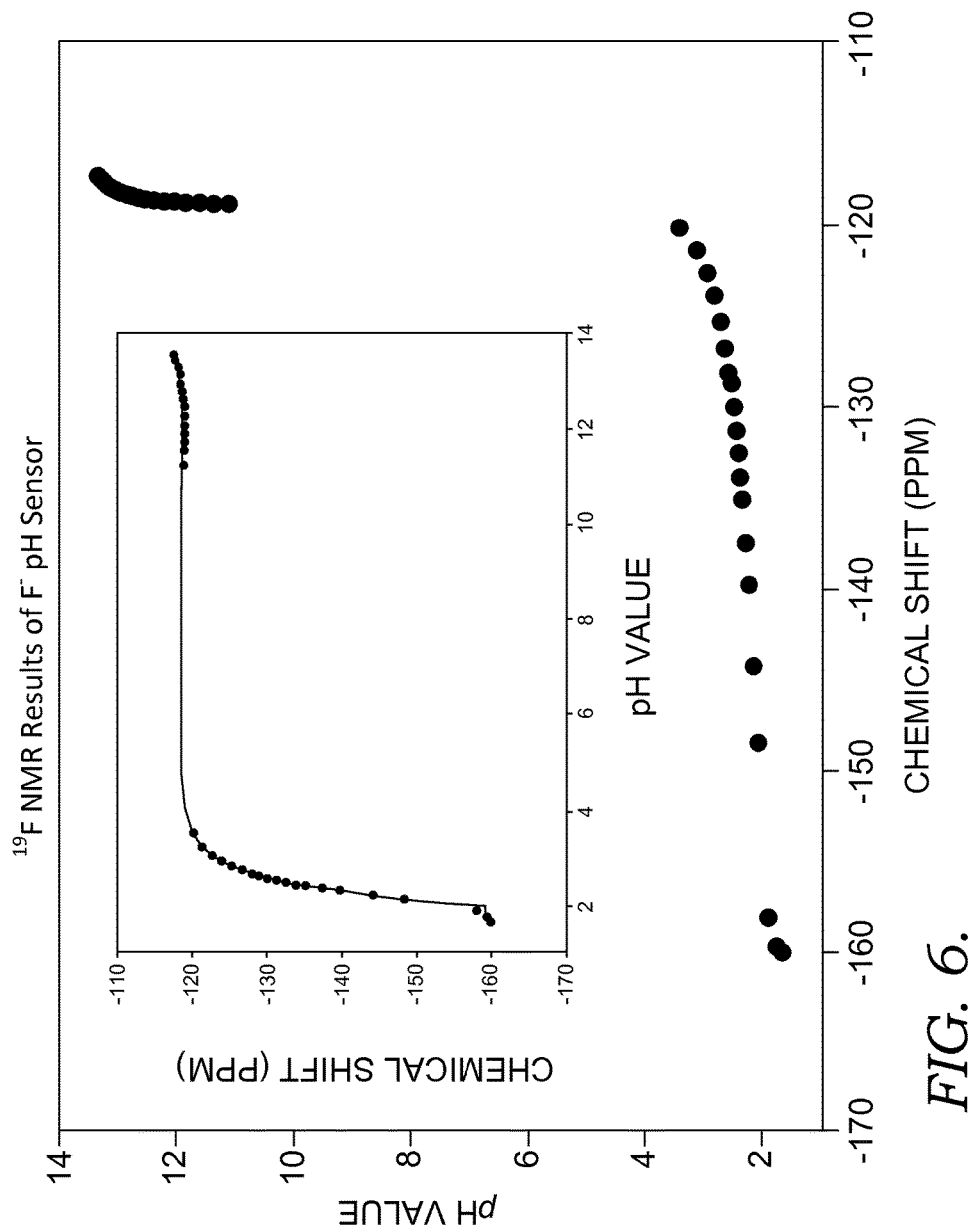
FIG. 6 is a plot of $^{19}F$ pH as a function of chemical shift of a solution of NaF in $D_2O$ as described in Example 2, according to one embodiment described herein.

FIG. 6 depicts a plot of pH as a function of the 19F chemical shift for an acidic and basic solution of 7 milligrams of NaF in 600 microliters of D$_2$O. The acidic solution was made using 2.5 microliter additions of 0.001 molar HCl from pH 1.7 to pH 3.5. The basic solution was made using 2.5 microliter additions of 0.005 molar NaOH from pH 11.0 to pH 13.5. The inset on the plot shows 19F chemical shift as a function of pH and the equation that was used to fit the data points. The change of NaF chemical shifts from pH 1.7 to pH 4.5 varied greatly. In that range, a change in one or more decimal positions for the pH value was observed, e.g., a chemical shift of NaF between pH 4.40 and 4.41 was observed, as opposed to 4.4 to 4.5.

NMR spectra for the NaF pH sensor and a target molecule were obtained by preparing the NMR tube using 600 microliters of D$_2$O, 7 mg of NaF, and 3 microliters of the target molecule, 1,1,1,2,2-pentafluorododecan-3-ol. 2.5 microliters of 0.001 molar HCl solution was added to the NMR tube and the 19F NMR spectrum was recorded. This was repeated until a total of 42.5 microliters of HCl had been added to the tube, then two additions of 10 microliters of the HCl solution were performed, followed by three 50 microliter additions of the HCl solution until a total of 212.5 microliters of the HCl solution had been added. After each HCl addition, the target sample in the NMR tube was measured with an electronic pH meter.

Another NMR tube was prepared using 600 microliters of D$_2$O, 7 mg of NaF, and 3 microliters of 1,1,1,2,2-pentafluorododecan-3-ol. 2.5 microliters of a 0.005 molar NaOH solution was added to the NMR tube and the 19F NMR spectrum was recorded. This was repeated until a total of 20 microliters was added, then 10 microliter portions of the NaOH solution was added until a total of 80 microliters of NaOH had been added to the NMR tube, followed by addition of 100 microliter portions of the NaOH solution until a total of 1080 microliters of the NaOH solution had been added to the NMR tube. After each NaOH addition, the target sample in the NMR tube was measured with an electronic pH meter.

Figure 7A:
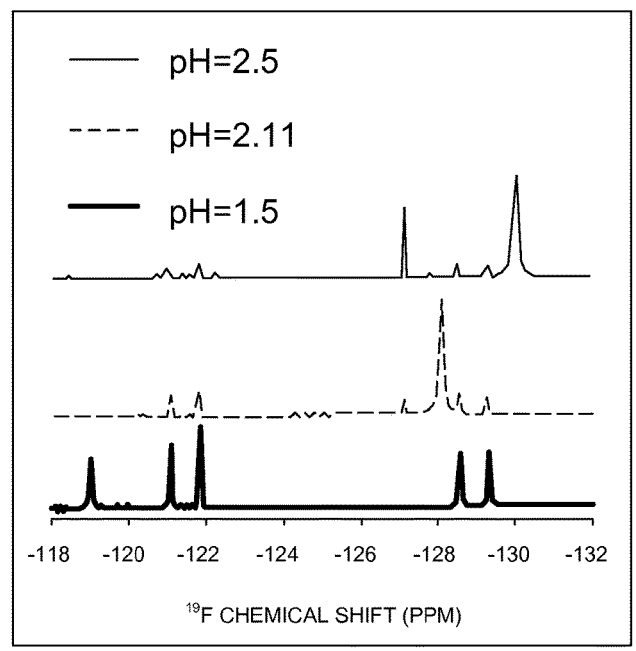
FIGS. 7A and 7B are $^{19}F$ NMR spectra of pH test molecule 1,1,1,2,2-pentafluorododecan-3-ol with NMR pH sensor NaF for two ranges of pH as described in Example 2, according to one embodiment described herein.

FIG. 7A depicts the 19F NMR spectrum of NaF for a multitude of different structural forms depending on the pH of the acidic target solution. For example, one form of the pH sensor probe molecule is represented by an NMR peak at approximately −119 ppm for pH 1.5; a different structural form of the pH sensor molecule is depicted by an NMR peak at approximately −128 ppm for pH 2.11. FIG. 7A also shows the 19F NMR spectrum of the pH sensor probe molecule at approximately −130.5 ppm for pH 2.5.

Figure 7B:
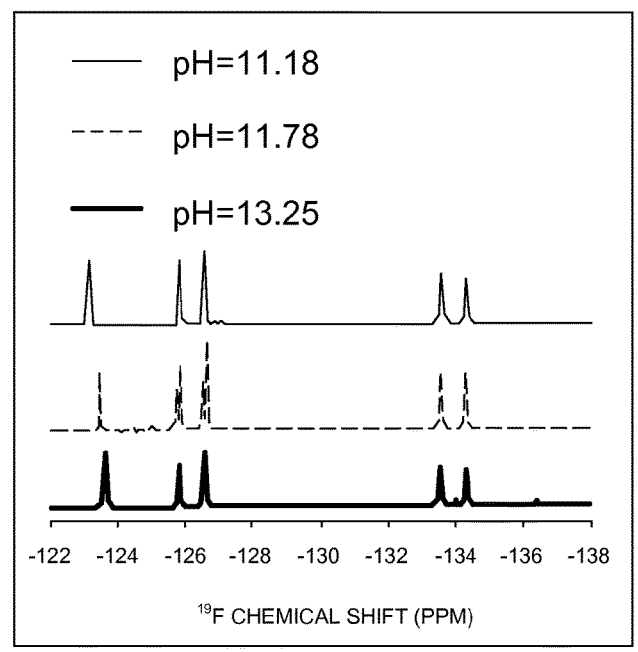

FIG. 7B depicts the 19F NMR spectrum of NaF for a multitude of different structural forms depending on the pH of the basic target solution. For example, one form of the pH sensor probe molecule is represented by an NMR peak at approximately −123 ppm for pH 11.18; a different structural form of the pH sensor molecule is depicted by an NMR peak at approximately −123.5 ppm for pH 11.78. FIG. 7B also shows the fluorine NMR spectrum of the pH sensor probe molecule at approximately −123.75 ppm for pH=13.25.

FIGS. 7A and 7B also include the 19F NMR spectra of the target sample material analyte molecule (1,1,1,2,2-pentafluorododecan-3-ol) for multiple pH environments. The 19F NMR spectrum of the target sample material analyte in FIG. 7A is revealed by a set of five NMR peaks at approximately −121, −122, −127, −128.5, and −129.5 ppm. The 19F chemical shifts have shifted to the right for different pH values and the target sample peaks have changed. The 19F NMR spectrum of the target sample material analyte molecule (1,1,1,2,2-pentafluorododecan-3-ol) in FIG. 7B is revealed by a set of four NMR peaks at approximately −126, −126.5, −133.5, and −134.5 ppm. The 19F chemical shifts have shifted to the left for different pH values and the target sample peaks have not changed.

Figure 8:
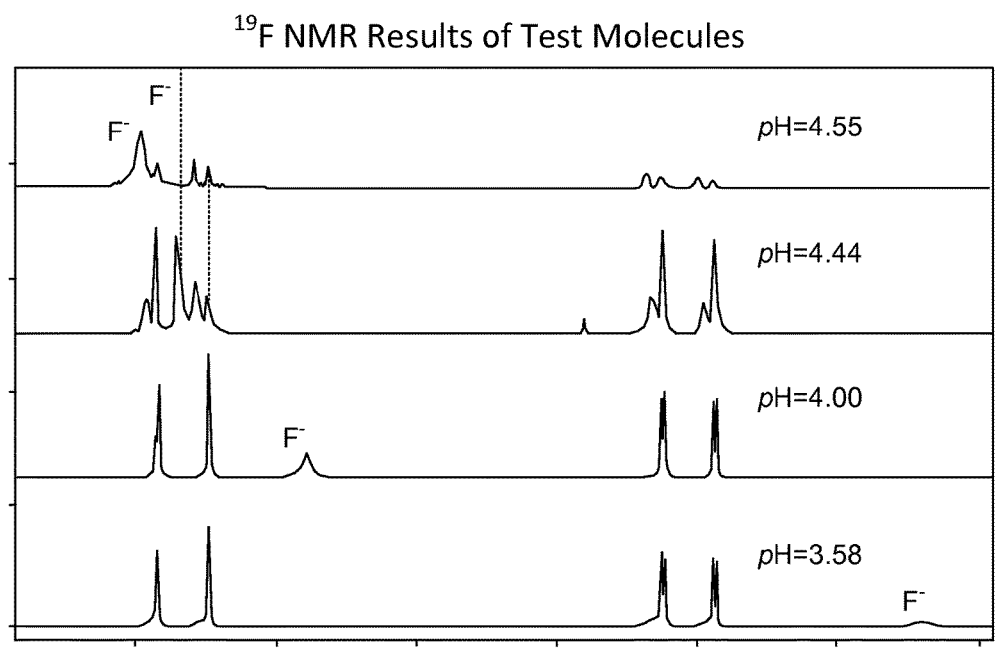
FIG. 8 is $^{19}F$ NMR spectra of pH test molecule 1,1,1,2,2-pentafluorododecan-3-ol at various pHs as described in Example 2, according to one embodiment described herein.

FIG. 8 depicts the 19F NMR spectra of the target sample material analyte molecule (1,1,1,2,2-pentafluorododecan-3-ol). Peaks changed with NMR pH sensor peak (NaF) for four different pH values. When the pH was 3.58 and 4, the peaks for the target sample analyte did not change much. When the pH was 4.44 and 4.55 the target sample analyte peak changed to indicate two separate molecular species.

Measurements of the 19F chemical shifts for NaF can be used in conjunction with a calibration curve shown in FIG. 6 to determine the pH of the solutions of target sample material analyte molecules. A mathematical correlation function was used to calculate pH from a 19F peak chemical shifts of the NaF pH sensor molecule. The pH was corrected for temperature variation. This example provides the paradigm for in situ monitoring of pH by 19F NMR spectroscopy via chemical shifts with the advantage of a spectral pH imprimatur.

Example 3: Using an In Situ Temperature Sensor to Measure the Activation Energy of the Conformation Change of DPPH External in situ temperature monitoring during NMR test of 2,2-diphenyl-1-picrylhydrazine (DPPH) in $CDCl_3$. The external in situ temperature sensor device was made of a sealed capillary tube (75 um internal diameter, 364 um outer diameter, 6 cm length). The capillary tube was filled with 100% ethylene glycol. The external in situ temperature sensor device was assembled similar to that depicted in FIG. 2. For example, the external in situ temperature sensor device was inserted into a 5-mm NMR tube, which was filled with DPPH solution. The external in situ temperature sensor device monitored the actual temperature of the DPPH sample in situ, and provided a temperature imprimatur. That is, the raw data/NMR spectra of the DPPH also includes the data of the ethylene glycol external in situ temperature sensor.

Figure 9:
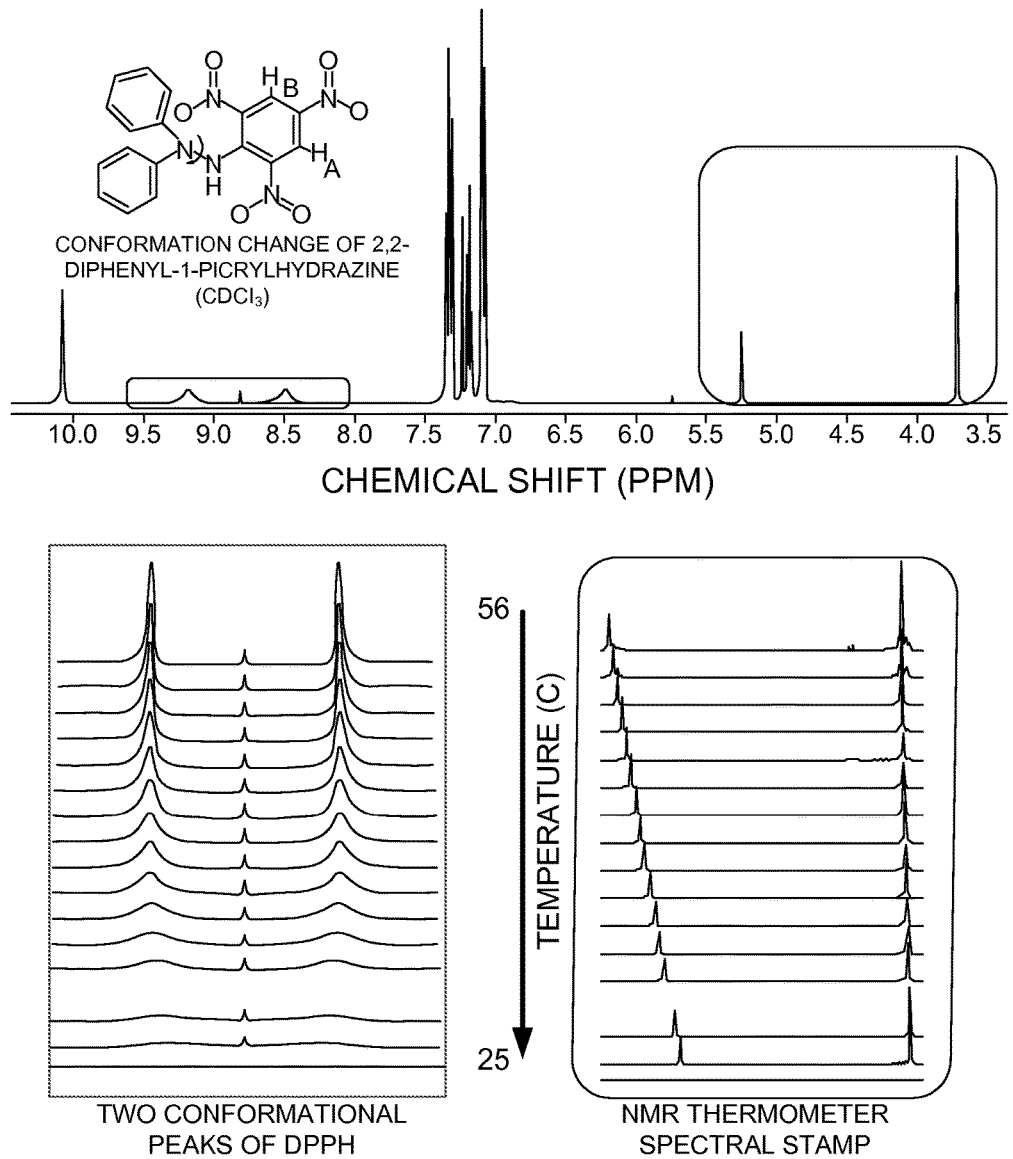
FIG. 9 depicts the NMR spectra of 2,2-diphenyl-1-picrylhydrazine at various temperatures using an in situ temperature sensor as described in Example 3, according to one embodiment described herein.

In this example, NMR spectra were recorded for DPPH sample (and the ethylene glycol external in situ temperature sensor) at temperatures from 25-56° Celsius in 2° Celsius increments. FIG. 9 shows a full exemplary spectrum with the box on the left highlighting to the two conformational peaks of DPPH and the box on the right highlighting the in situ thermometer spectral stamp (of ethylene glycol). Below the full spectrum is the individual spectrum at various temperatures in 2° increments (between 25-56° Celsius). By conducting a one pulse experiment, two peaks were successfully observed to reveal the conformational exchange of DPPH, and the two peaks of ethylene glycol that provided the temperature measurement. This data shows how the conformational change of DPPH correlates with various temperatures of the DPPH, as evidenced by the spreading out of the two prominent spectral peaks in the in situ thermometer containing ethylene glycol.

The proton NMR spectrum of ethylene glycol reference material can be used to determine the actual temperature of the ethylene glycol reference material, and of the DPPH, as they are in the same thermal environment of the in situ thermometer device. For example, a proton NMR spectrum of the ethylene glycol reference material contained in the capillary tube produces two sharp peaks. The separation of the two peaks measured in frequency units of Hz is entered into a standard published temperature calibration formula specific to ethylene glycol. The formula generates a numerical output that is the temperature of the ethylene glycol, capillary tube and surrounding sample.

Figure 10:
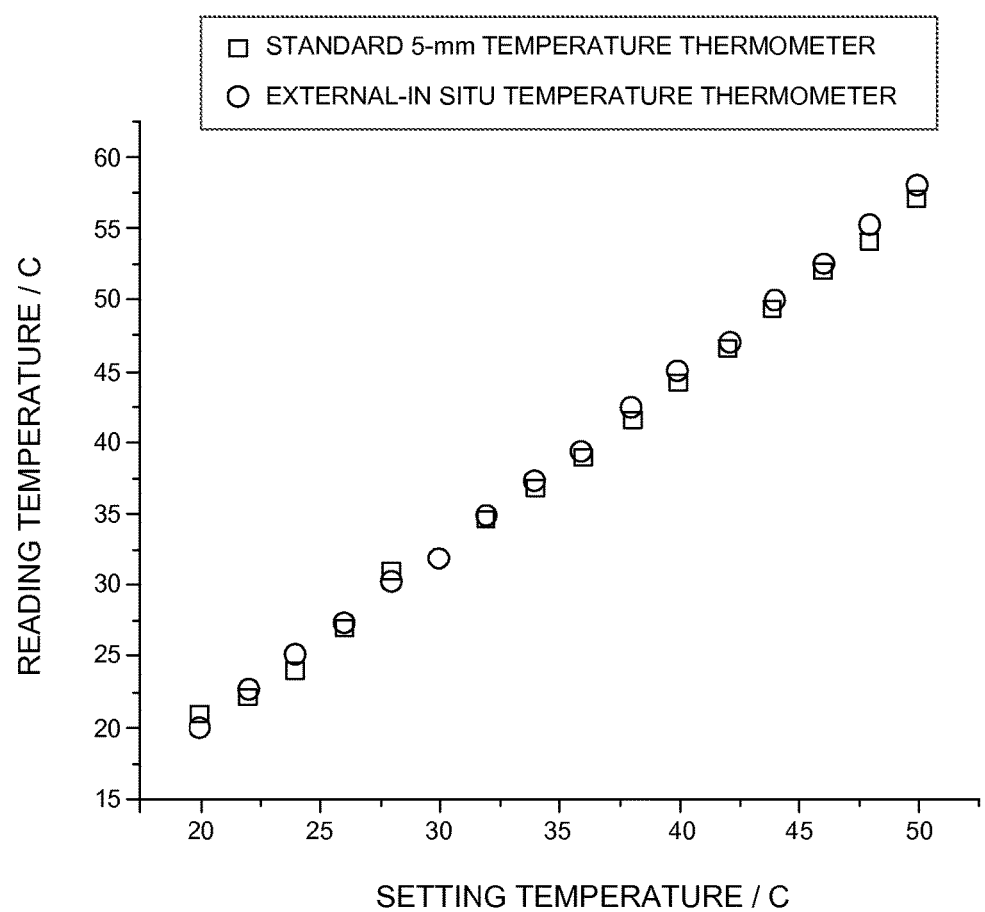
FIG. 10 is a plot of the setting and reading temperatures of ethylene glycol using a commercially available temperature probe and the in situ temperature sensor as described in Example 3, according to one embodiment described herein.

FIG. 10 depicts a graph comparing the temperature determined for the in situ temperature sensor used in this Example 3 with the temperature determined using a commercial NMR thermometer device. As can be seen in FIG. 10, the in situ temperature sensor used in this Example 3 produces similar temperature results as that using a commercial NMR thermometer.

Example 4: In Situ Temperature Monitoring During NMR Test of a Solid Sample

External in situ temperature monitoring during NMR test of a solid sample. The in situ temperature monitoring device was made of a sealed capillary tube (75 micrometer internal diameter, 364 micrometer outer diameter, 1 centimeter length). The capillary tube was filled with 100% ethylene glycol.

The MAS rotor and in situ temperature monitoring device were assembled similar to that described with respect to FIG. 3. For example, the MAS rotor contained a powder target sample illustrated. The plastic tube can be made of a polymer that is the target sample material that is to be analyzed for composition of plasticizer, for example. The 1 mm NMR tube is made of glass and is used as an element to keep the target sample and the NMR thermometer sensor centered so that the rotor will maintain balance during high speed rotation. Any cylindrical element made of a material that does not produce an NMR signal that will interfere with the NMR signals from the target sample is suitable (glass, ceramic tubes, etc.) can be used for this purpose. The MAS rotor itself is made of a ceramic (zirconia) and it does not produce NMR signals that interfere with the NMR signals produced by the target sample material. The arrangement of the target sample material, the cylindrical spacer element, the NMR capillary thermometer should be arranged so as to produce a rotationally-balanced system within the rotor, so cylindrical symmetry is not absolutely necessary. This embodiment has cylindrical symmetry. A cap is placed on the rotor to seal in the contents. The rotor is placed in the MAS probe.

The in situ temperature monitoring device monitored the actual temperature of the sample in situ, and provided a temperature imprimatur. Air jets were used to cause the rotor to spin at from 1-14 kHz in the. A one-pulse experiment during MAS was conducted.

Figure 11:
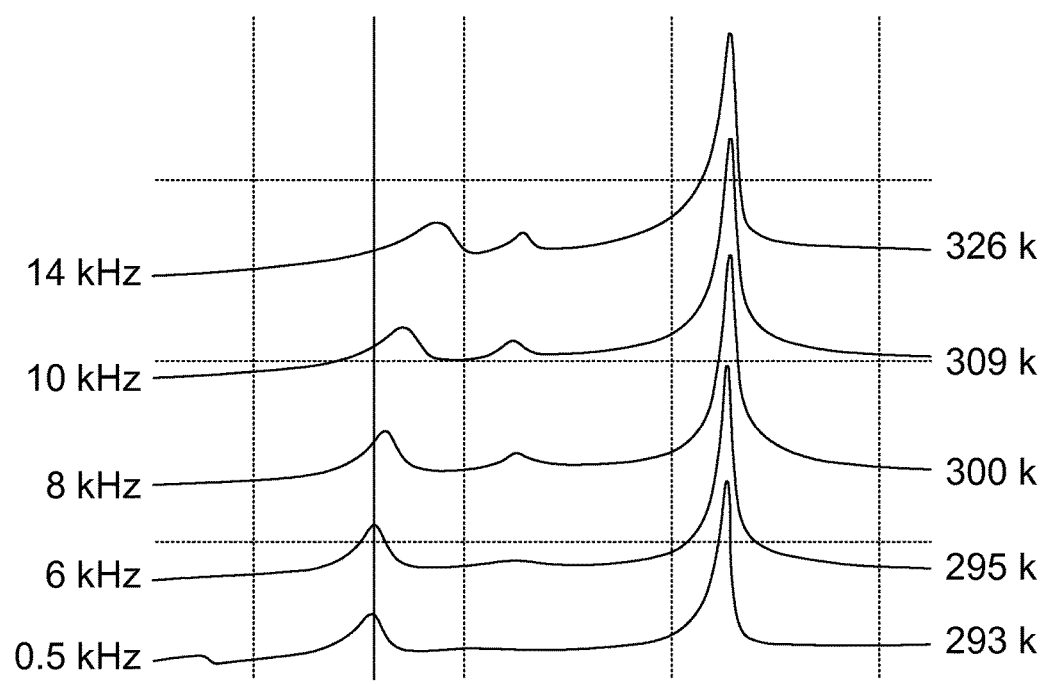
FIG. 11 is NMR spectra of a solid sample using an in situ temperature sensor as described in Example 4, according to one embodiment described herein.
Figure 12:
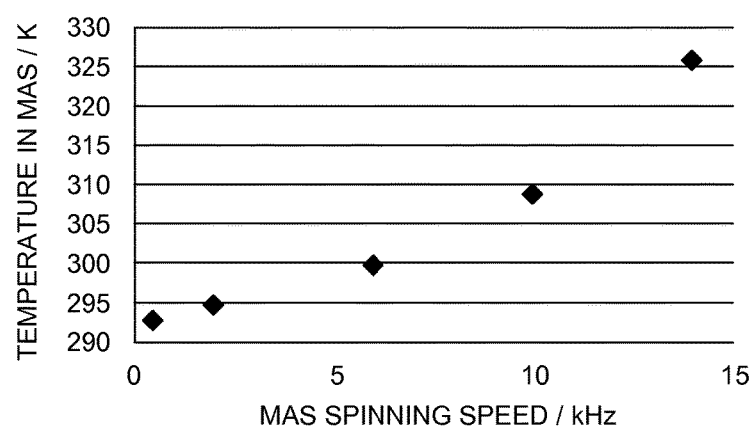
FIG. 12 is a plot of the spinning speed of the MAS rotor and the temperature of the reference material, and a numerical table is also provided for this graph, as described in Example 4, according to one embodiment described herein.

FIG. 11 shows a set of stacked spectra that reveal the temperature as metered by the thermometer and indicated by the difference between left most peak (with the vertical line) and the right most sharper peak as measured in Hz or PPM. This difference is entered into a well-known equation that outputs the temperature at the location of the NMR thermometer sensor. The temperature is indicated at the right. As the rotation speed of the rotor increases, the two peaks come closer together. The equation takes in the separation of the two peaks in Hz or PPM and outputs the temperature of the NMR temperature sensor in Kelvins. The bottom axis of the NMR plots is Hz or PPM. The temperature of the rotor increases with spinning speed as shown in FIG. 12, which is a plot of the temperatures of the NMR thermometer sensor molecule as a function of spinning speed.

Example 5: Identification of a $^{11}B$ Integrated Reference Sample in an In Situ Measuring Device for an MAS Rotor The in situ measuring device used in this example included a sealed capillary tube positioned inside a solid state NMR rotor, such as that depicted in FIGS. 13A, 13B, and 14. Specifically, as described in this Example 5 further below, the sealed capillary tube having an internal diameter of 1.2 millimeter contained a 1.0 M boric acid solution (anhydrous boric acid dissolved in DMF) or was left empty, and the top of the capillary tube was sealed with Teflon tape. The sealed capillary tube was placed in a solid state NMR rotor to form an in situ measuring device.

The in situ measuring device was then inserted in an MAS rotor and $^{11}$B NMR spectra were recorded. Specifically, the in situ measuring device and MAS rotor were positioned and spun at the magic angle, θm (54.74°), inside the static magnetic field with respect to the direction of $B_0$, which narrows the NMR peaks. In order to compensate for the lack of molecular motion in solid samples, MAS was developed to remove the anisotropic interactions. MAS is the rapid mechanical rotation of the whole sample at the "magic angle," with respect to the external magnetic field. MAS decouples CSA and weak homo-nuclear and/or hetero-nuclear dipolar coupling to provide a well resolved spectrum; spinning sidebands are reduced in intensity with increasing spinning speed. However, the strong centrifugal force caused by magic angle spinning in MAS rotors makes it impossible to have a fluid reference material in an external integration standard for quantitative MAS-NMR determination because the fluid is made to have high pressure and flow out of the MAS rotor.

Figure 15:
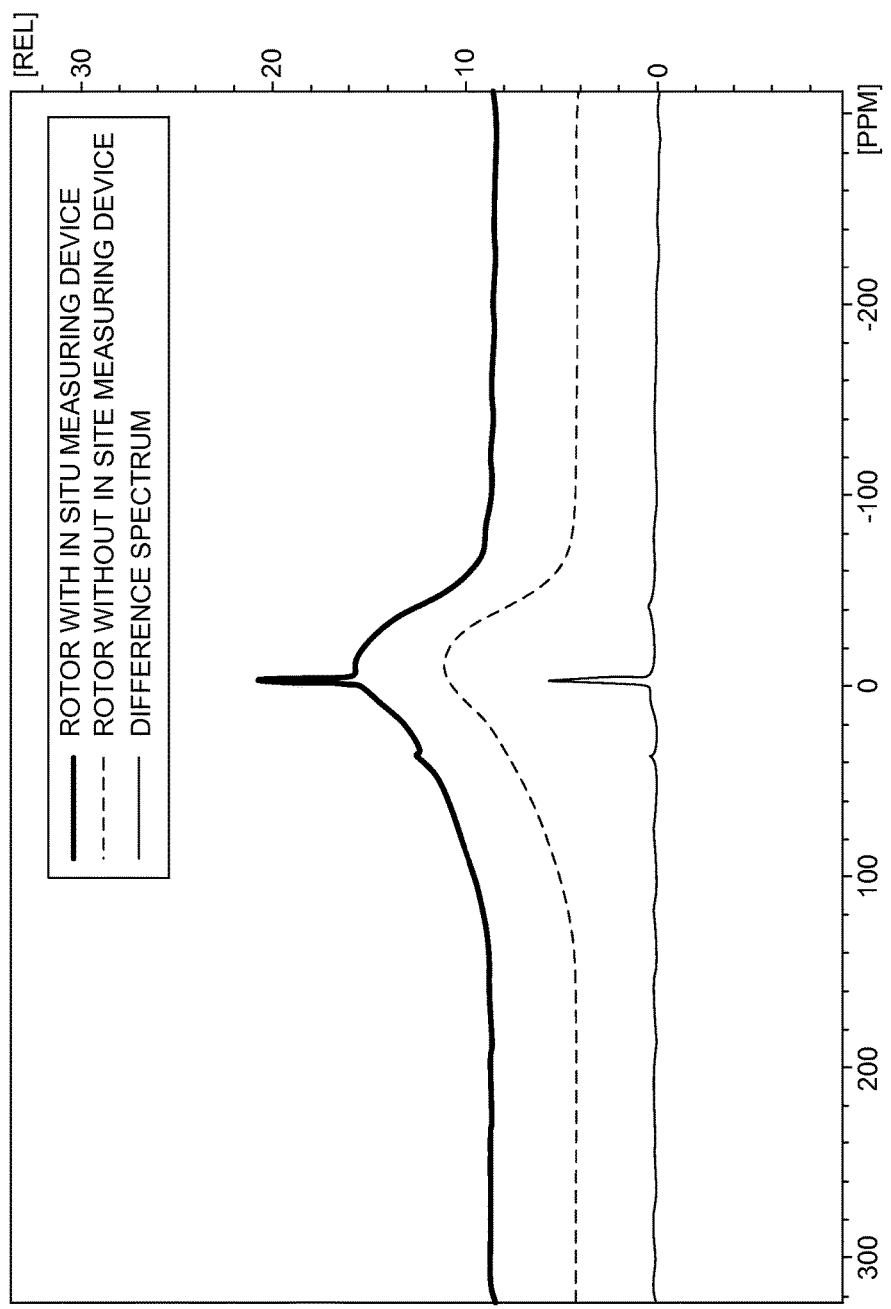
FIG. 15 is a plot of the $^{11}B$ solid state NMR spectra of the in situ measuring device described in Example 5 with and without an empty capillary tube, and further shows the difference spectrum, according to one embodiment described herein.

FIG. 15 depicts the $^{11}$B solid state NMR spectra of the MAS rotor with and without the capillary tube, which is empty. Further, FIG. 15 illustrates the difference spectrum of the two aforementioned spectra. By comparing these three NMR spectra, one can discern that the difference spectrum represents the $^{11}$B spectrum of the empty capillary tube, which can be used as an integration and/or chemical shift reference sample peak.

Figure 16:
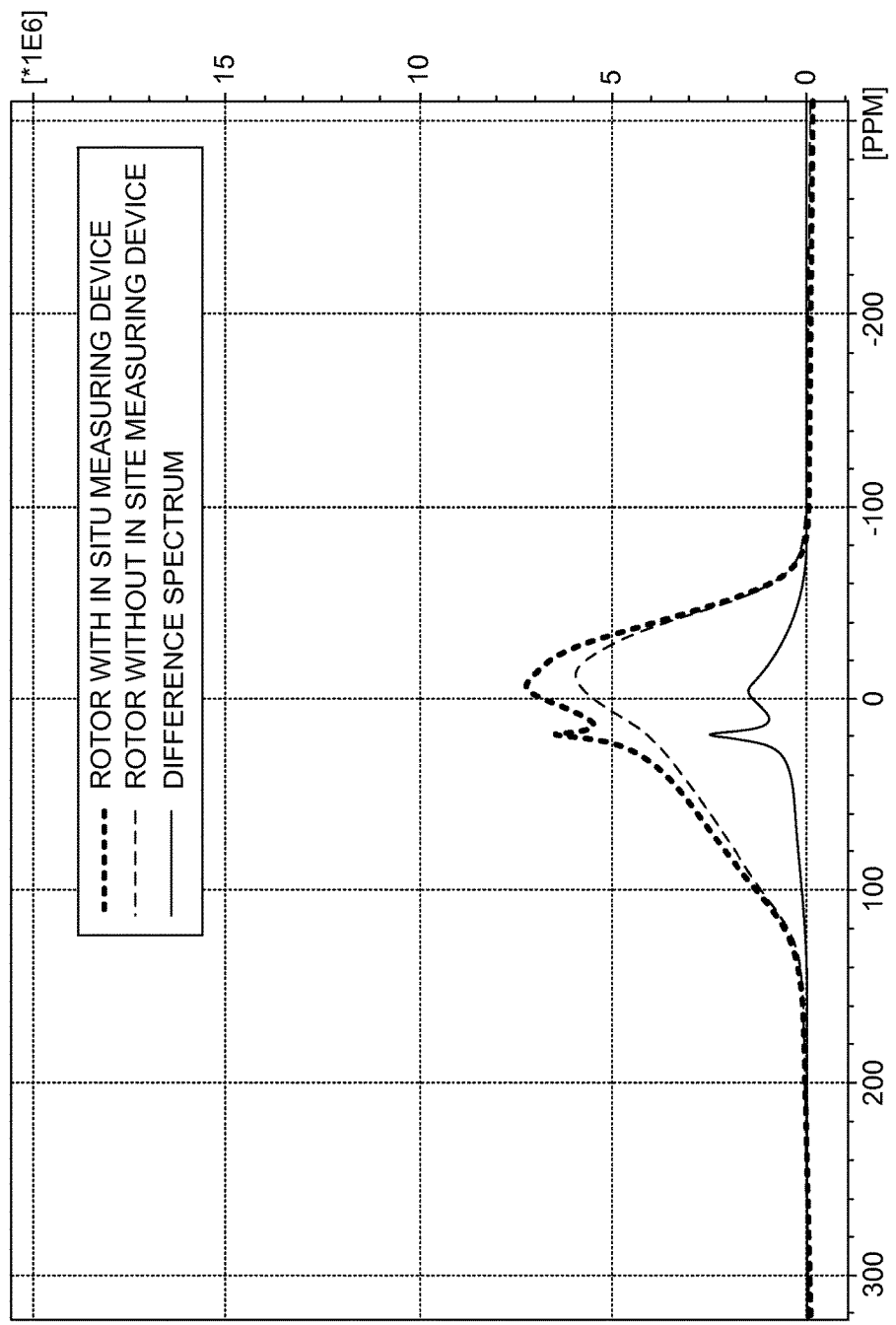
FIG. 16 is a plot of the $^{11}B$ solid state NMR spectra of the in situ measuring device described in Example 5 with and without the capillary tube filled with a boric acid/DMF solution, and further shows the difference spectrum, according to one embodiment described herein.

FIG. 16 depicts the $^{11}$B solid state NMR spectra of the MAS rotor with and without the capillary tube, where the capillary tube is filled with a boric acid/DMF solution, as described above. The difference spectrum shown in FIG. 16 represents the $^{11}$B spectrum of the substance that composes the capillary tube, as well as, boric acid inside the capillary tube. Comparing the difference spectrum from FIGS. 15 and 16, which shows the spectrum of the capillary tube without and with the boric acid/DMF solution, respectively, one can discern that the sharp signal on the left shoulder of the difference spectrum for the capillary tube with the boric acid/DMF solution depicted in FIG. 16 is indicative of the empty capillary tube. The broad peak on the right of the sharp peak results from a target sample material in the unknown sample material that simultaneously occupies the MAS rotor.

In addition, the in situ measuring device was prepared as described above with varying materials in the sealed capillary tube (or nothing) and with varying materials or nothing in the rotor. Table 1 below shows the five particular in situ measuring devices examined.

Figure 17:
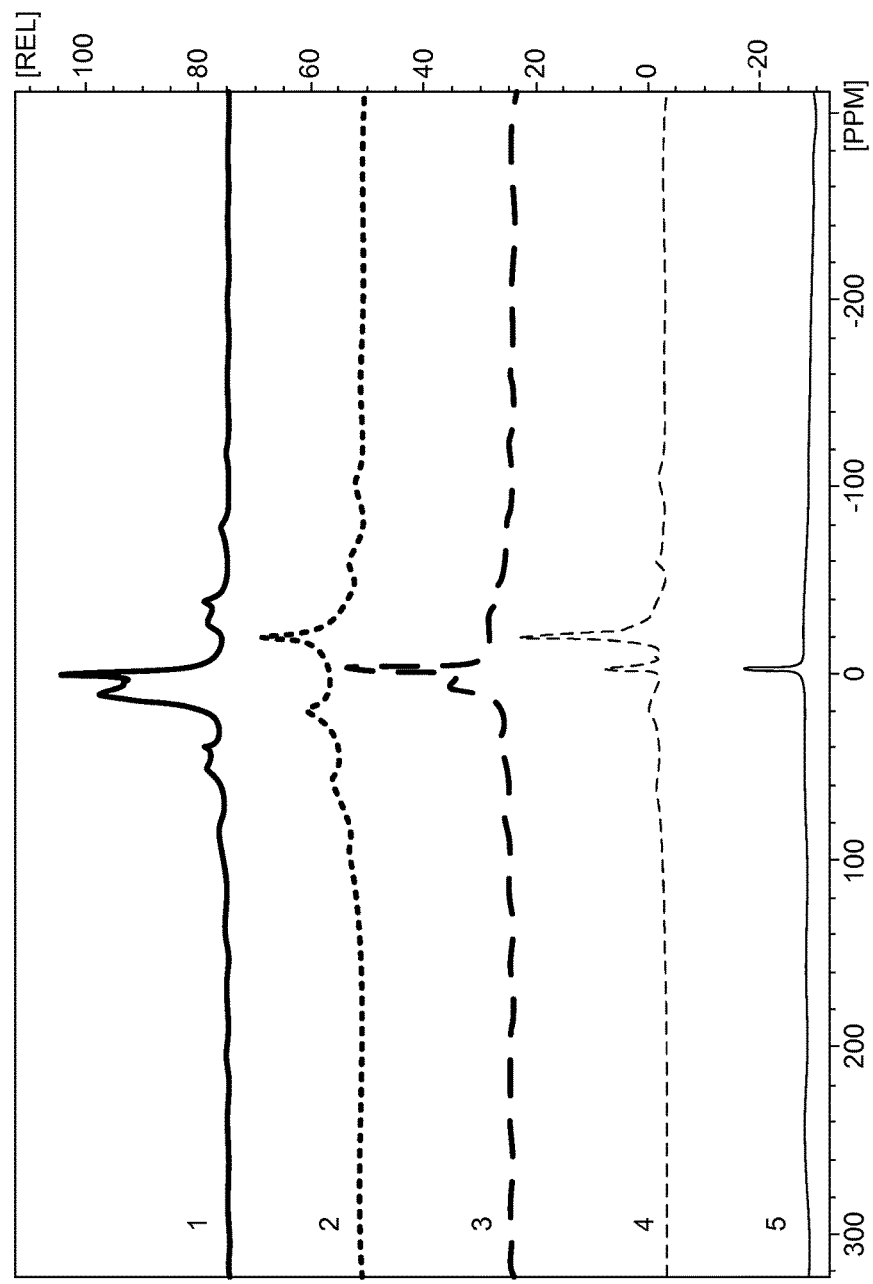
FIG. 17 is a plot of $^{11}$B solid state NMR spectra of the in situ measuring device described in Example 5, where the capillary tube and/or MAS rotor are filled with various materials or empty as described in Table 1, according to one embodiment described herein.

TABLE 1 in situ measuring devices for $^{11}$B NMR spectra in FIG. 17

| Spectrum | Sample in capillary tube | Sample in MAS rotor |
| --- | --- | --- |
| 1 | Empty (capillary tube) | Boron Amide |
| 2 | Dodecaborane | Empty (rotor) |
| 3 | Ground glass (no capillary tube) | Empty (rotor) |
| 4 | Boric Acid/DMF | Boric Acid Anhydrous |
| 5 | Empty (capillary tube) | Empty (rotor) |

As can be observed from the $^{11}$B NMR spectra in FIG. 17, that of the five in situ measuring devices tested, the best $^{11}$B NMR spectra in situ reference material is an empty capillary tube (single, sharp, easily discernable peak). However, such an in situ reference standard cannot be utilized, because the sharp $^{11}$B signal is present at the same location that many other $^{11}$B signals are observed, as can be seen in FIG. 17. NMR spectra overlapping $^{11}$B signals (or NMR signals in general) cannot be easily used for quantitative determination. Yet, these experiments in Example 5 do demonstrate that by using an empty capillary tube in an in situ measuring device, and running MAS-NMR experiment with signal subtraction, a single narrow $^{11}$B peak was successfully observed and is useful for many samples that do not show overlapping peaks in their corresponding NMR spectra.

Example 6: Using In Situ Measuring Device to Determine the Quantity of a Target Sample In this Example 6, an in situ measuring device was used to measure the number of protons in a target sample (rubber band in this case). Generally, in this Example 6, the in situ measuring device included a sealed capillary tube with a known amount of a reference material positioned inside a MAS rotor, with the target sample positioned inside the MAS rotor, around the capillary tube. The in situ measuring device was substantially similar to that depicted in FIGS. 13A and 13B, and discussed in detail above.

Specifically, the in situ measuring device was fabricated by cleaning a closed-ended glass capillary reference tube with dimensions 1 millimeter internal diameter, 1.5 millimeter outer diameter, and 13 millimeter length using acetone, followed by air drying. The glass capillary reference tube was weighed five times to determine its mass and mass uncertainty as 6.100+/−0.002 mg. Commercially available high-purity ethylene glycol was placed inside the glass capillary reference tube to fill the bottom half portion of the container.

The glass capillary reference tube was then flame sealed using a commercially available micro torch. Particularly, the open end of the glass capillary reference tube was concentrically mounted at the top of the spindle of a commercially available stepper motor. A thin metal plate was prepared with a hole 1.6 millimeter in diameter and positioned above the stepper motor such that the glass capillary reference tube passed through the hole in the metal plate and extended above the metal plate by 1 millimeter.

The stepper motor was activated and caused the glass reference capillary tube to rotate at 2-4 revolutions per second. The intense blue flame of the micro torch burning a combustible gas was aimed at the 1 millimeter portion of the glass reference capillary tube that extended above the metal plate. The metal plate prevented the flame and heat from impacting the portion of the glass reference capillary tube that contained the ethylene glycol and that was positioned below the metal plate. A stream of very cold nitrogen gas was directed at the portion of the glass capillary reference sample tube that is located below the metal plate for the purpose of cooling the glass capillary reference sample tube and the ethylene glycol. The purpose of cooling the reference sample was to prevent evaporation and degradation caused by the high temperatures from the glass sealing process. Cooling of the glass capillary reference sample tube can be performed to maintain the reference material at temperatures above, below or at room temperature. It may be advantageous to maintain the temperature of the reference material below its freezing point so that very little volatility occurs. The cooling gas was applied to the bottom of the glass reference capillary tube after the flame was applied to the top of the tube. Using this sequence, the mixture of reference sample vapor and air (located above the liquid reference sample), which may contain water vapor and other gaseous impurities, were caused to be excluded from the glass capillary reference sample tube before it was completely sealed. Continuous or intermittent applications of the flame to the top, open portion of the glass reference capillary tube, that was made to rotate by the stepper motor, caused the glass to melt and close the tube opening. At the moment that the seal was fully formed, the flame was turned away from the glass reference tube. The soft molten glass formed a small expanded bubble that was approximately 2 millimeters in diameter. The bubble was formed by the residual gases that were trapped and heated inside the top of the reference capillary tube. The glass capillary reference sample tube was allowed to cool to room temperature with intermittent applications of heat for purposes of annealing the glass bubble.

The half-filled and sealed glass capillary reference sample tube was then weighed and its mass was 13.785+/−0.002 milligrams. The mass difference between the empty capillary reference sample tube and the capillary reference sample tube half-filled with high-purity ethylene glycol was, therefore, the mass of the ethylene glycol reference material, 7.685+/−0.002 milligrams. As can be seen in Table 2, the number of corresponding moles of ethylene glycol was 0.000124+/−0.000002 moles, and the corresponding moles of methylene protons measured for the ethylene glycol was four times larger, 0.000495312+/−0.000002 moles.

TABLE 2

Ethylene Glycol Amounts and Properties
Ethylene Glycol

| Molar mass (g · mol$^{-1}$) | Mass (mg) | Mass(g) |
|---|---|---|
| 62.07 | 7.686 +/− 0.002 | 0.007686 |
| Number of moles in $CH_2$ group | Number of mole of protons in $CH_2$ group | Moles of Ethylene Glycol |
| 0.000248 | 0.000495312 | 0.000124 |

The number of moles of methylene protons in the glass capillary reference sample tube containing ethylene glycol was used to directly calculate the number of protons of all chemical types in the target sample material of the unknown sample, in this case, a rubber band. Because the glass capillary reference sample tube was sealed, it can be used repeatedly for determining the total number of all types of chemical protons in a target sample material of an unknown sample.

The procedure used to measure the amount of protons of all chemical types contained in the target sample material of a rubber band sample (that includes isoprene, ethanol, and other compounds) included the steps of weighing the rubber band sample, placing the rubber band in the commercial MAS rotor container, arranging and packing the rubber band symmetrically around the glass capillary reference sample tube, and covering the commercial MAS rotor with a rotor cap. These steps were followed to symmetrically and evenly dispose the rubber band in the commercial MAS rotor with the glass capillary reference sample tube disposed in the center and along the center axis of the commercial MAS rotor.

An innocuous, non-protonic solid fine powder material, $B_2O_3$, was used to fill all empty space in the commercial MAS rotor. The $B_2O_3$ fine powder was symmetrically pressed into the commercial MAS rotor. A small piece of Kimwipe paper in the shape of a circle (with diameter of the commercial MAS rotor) was placed on top of the $B_2O_3$ to prevent shifting of the fine powder, and then the rotor cap was secured in place to contain all of the components and to prevent any materials from shifting positions inside the commercial MAS rotor during high speed rotation. The capped commercial MAS rotor was placed in the commercial MAS probe and rotated at 7000+/−1 Hz and the temperature of the commercial MAS probe was set and regulated at a probe temperature reading of 340.0+/−0.2K. Various multinuclear solid-state carbon and proton MAS NMR experiments were conducted on the sample to determine the identity, quantity, and temperature of a target sample material in the unknown sample.

Figure 18:
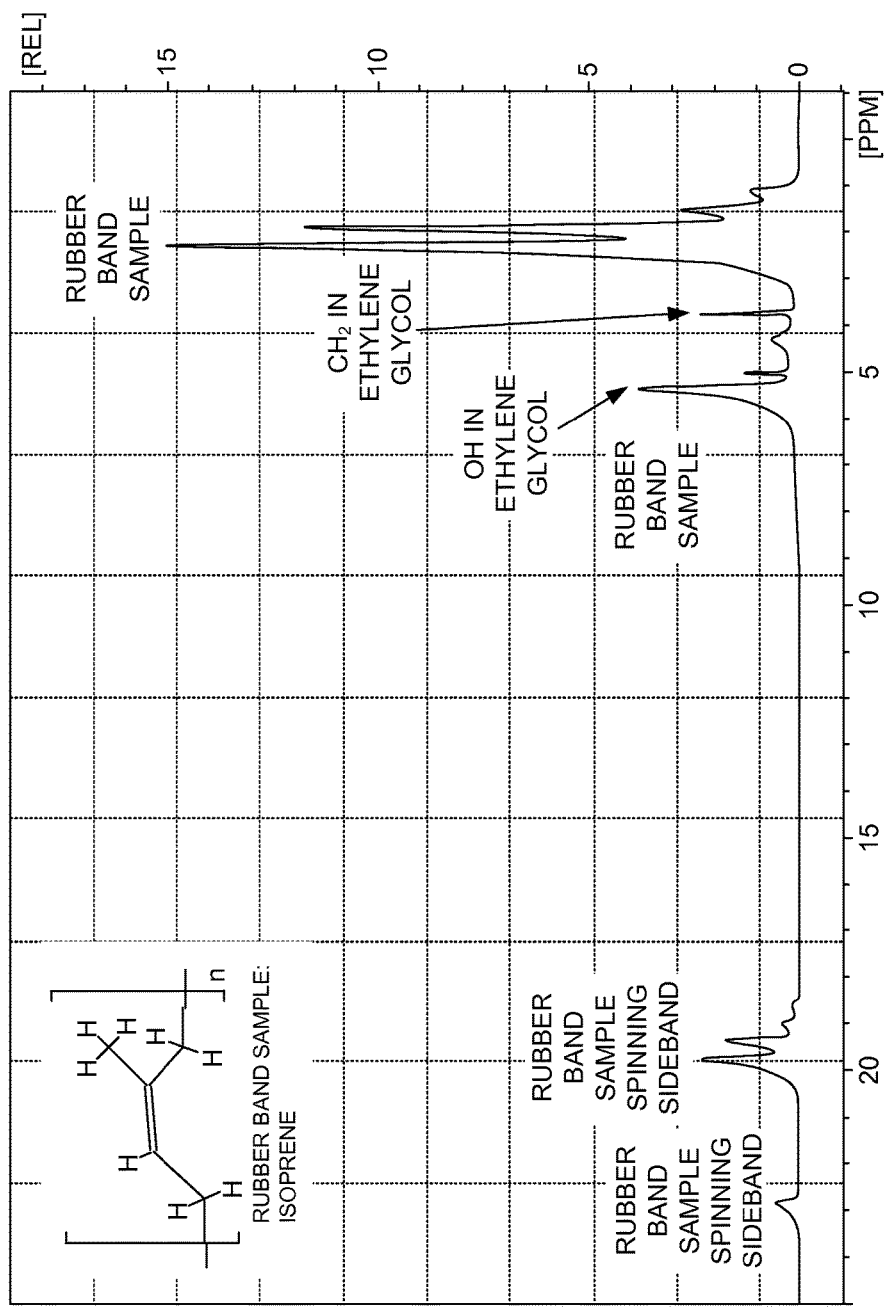
FIG. 18 is a plot of the proton solid state NMR spectrum of the in situ measuring device described in Example 6.

In this Example 6, to determine the quantity of all types of chemical protons contained in the target material of the rubber band, a proton solid-state MAS spectrum was recorded using a Bloch Decay pulse sequence experiment with a recycle delay of 10 seconds, a pulse width of 4 microseconds, and a total accumulation of 128 scans. The spectrum is depicted in FIG. 18. A Fourier Transform of the proton MAS NMR spectrum was performed by the commercial NMR spectrometer computer software and analyzed by performing standard baseline correction and integration procedures. The relative integration of the reference peak for $CH_2$ in ethylene glycol is 4.00. The total integration of all other peaks except OH peak of ethylene glycol was 202.6643. Given that the gravimetrically-determined absolute amount of $CH_2$ protons in the reference material inside the capillary tube was 0.0003329 moles, the total number of protons in the sample target materials contained in the rubber band sample was calculated to be 0.01687 moles. The explicit calculation was 0.0003329 mol*202.6643/4.00=0.01687 mol. Furthermore, the reference sample chemical shift secondary proton standard for $CH_2$ in ethylene glycol is 3.765 ppm. Measuring the chemical shift of the peaks for the target materials in the unknown rubber band sample, it was possible to obtain information of all the types of chemical protons present in the unknown rubber band sample. For example, a proton peak observed around 5.0-6.5 ppm is known in the art to correspond to a C$\underline{H}$=C type proton. Therefore, since in the spectrum of the unknown rubber band sample one peak was observed at 5.40 ppm, it was deduced that a CH=C group is a constituent chemical group in one or more of the target sample materials in the rubber band sample. In fact, the CH=C chemical group is known in the prior art to be found in isoprene.

TABLE 3

Determination of the Number of Protons in the Rubber Band Sample
Ratio of Ethylene Glycol ($CH_2$) with Rubber band: 4.000:202.6643

| Rubber Band Mass (mg): | Number of moles of protons in |
|---|---|
| 57.696 +/− 0.001 | rubber band: 0.01687 |

Figure 19:
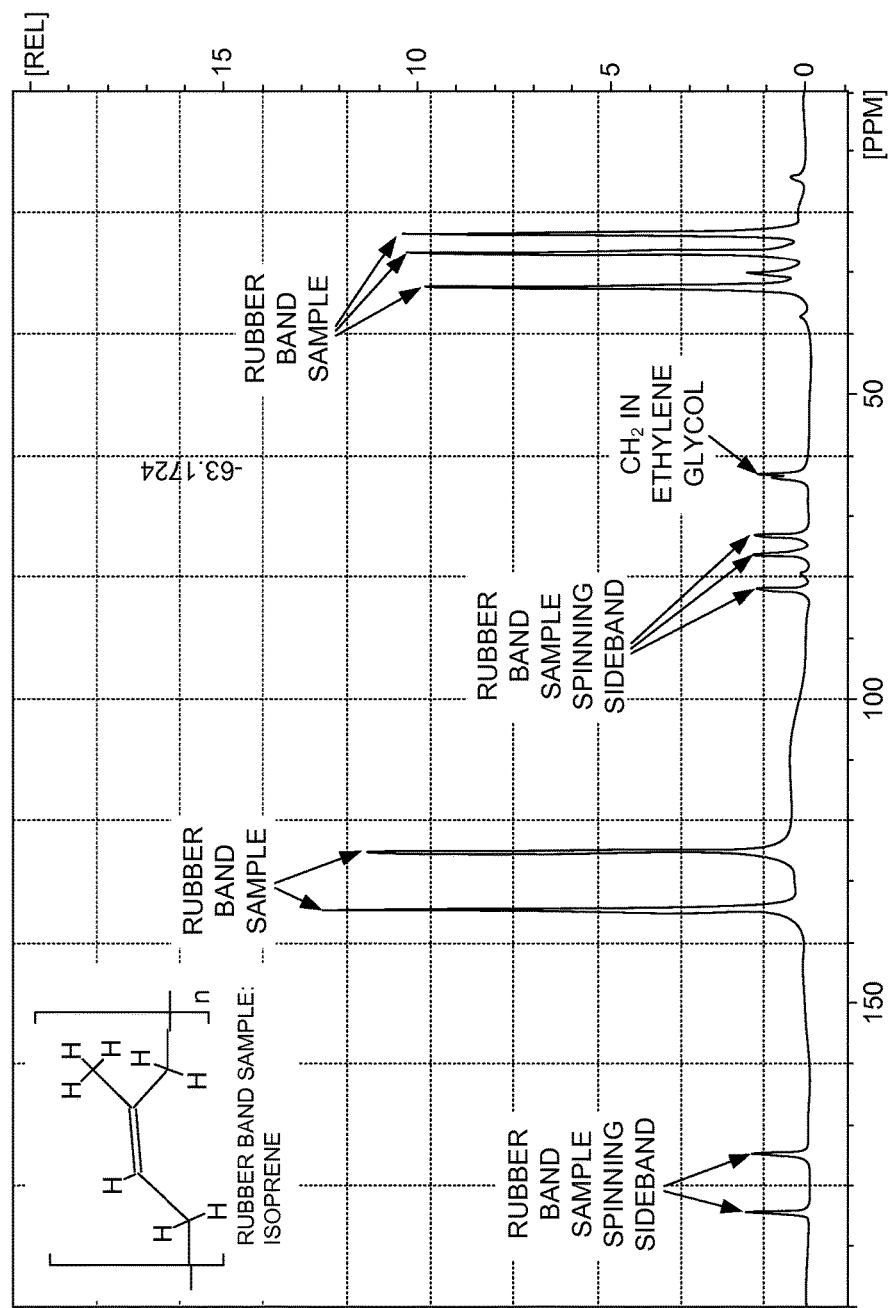
FIG. 19 is a plot of the carbon solid state NMR spectrum of the in situ measuring device described in Example 6 and 7.

Example 7: Using In Situ Measuring Device to Determine the Chemical Identity of a Target Sample In this Example 7, the in situ measuring device of Example 6 was used to determine the identity of chemicals contained in the target material of the rubber band target unknown sample. Specifically, a carbon solid-state MAS spectrum of the in situ measuring device of Example 6 was recorded using the Bloch Decay pulse sequence experiment with a recycle delay of 10 seconds, a pulse width of 4 microseconds, and a total accumulation of 1024 scans. The spectrum is depicted in FIG. 19. A Fourier Transform of the carbon MAS NMR spectrum was performed by commercial NMR spectrometer computer software and analyzed by performing standard baseline correction. The chemical shift axis of the carbon MAS NMR spectrum was calibrated to 63.1724 ppm by using the carbon resonance of the methylene group of the ethylene glycol reference standard in the capillary reference sample tube. According to the chemical shifts of carbon peaks known in the art, information of all types of chemical carbons in the rubber band sample were obtained. For example, the carbon types $\underline{C}H_3$, $\underline{C}H_2$—CH=C, $\underline{C}H$=C—CH$_2$, H$\underline{C}$=C and HC=$\underline{C}$ peaks were identified for the rubber band sample by observing the corresponding carbon chemical shifts at 23.28, 26.41, 32.15, 125.04 and 134.58 ppm, respectively. Alternative chemical shift assignments may also be possible according to what is known in the prior art. These peaks and their chemical shifts constitute unique and specific data that was used to characterize and define the target sample material of the rubber band sample.

Figure 20:
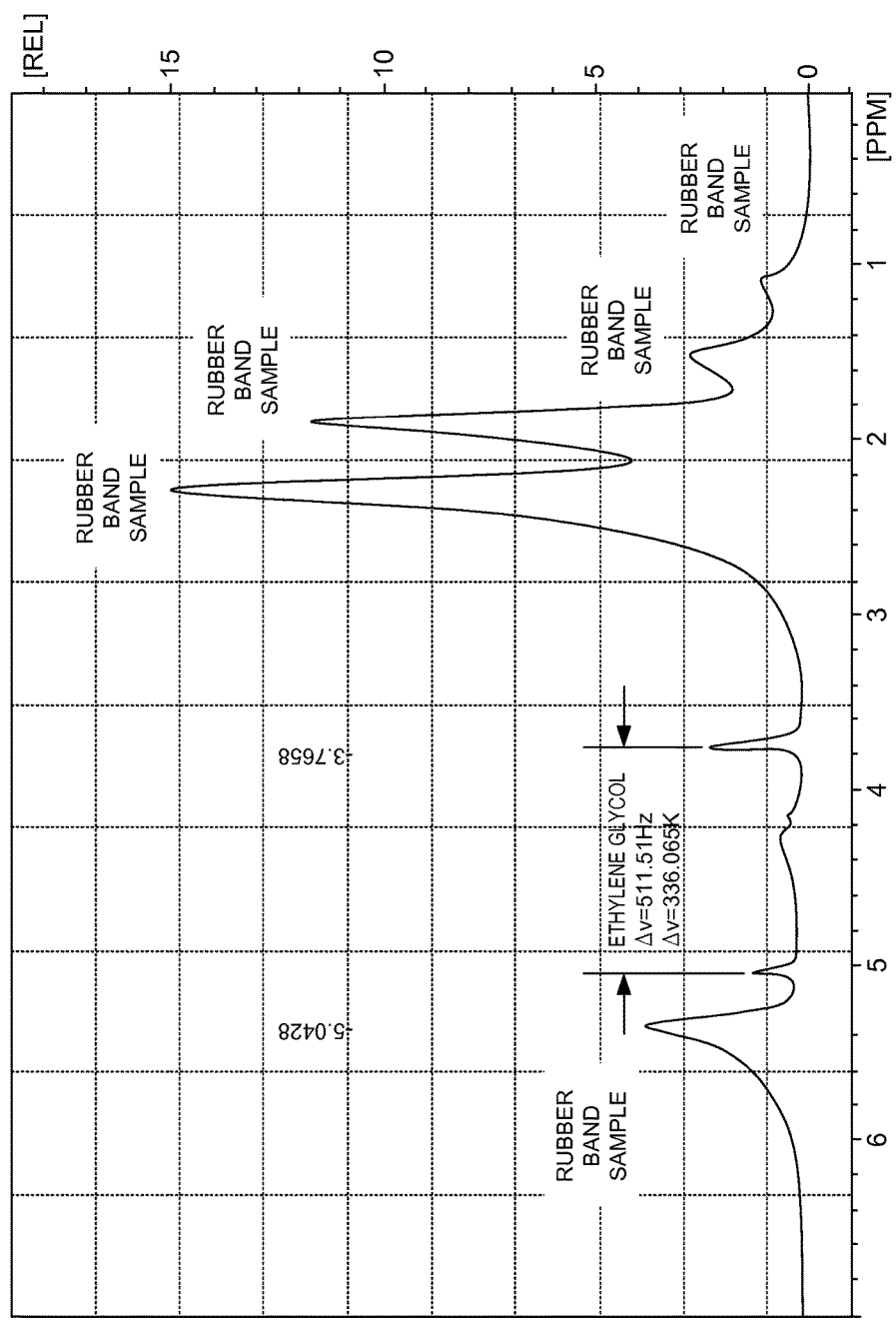
FIG. 20 is a plot of the proton solid state NMR spectrum of the in situ measuring device described in Example 6 and 8.

Example 8: Using In Situ Measuring Device to Determine the Temperature of a Target Sample In this Example 8, the in situ measuring device of Example 6 was used to determine the temperature of the target material of the rubber band target sample for the purposes of studying molecular dynamics, for example. Specifically, a proton solid-state MAS spectrum of the in situ measuring device of Example 6 was recorded using the Bloch Decay pulse sequence experiment with a recycle delay of 10 seconds, a pulse width of 4 microseconds, a total accumulation of 128 scans, and a rotor rotation speed of 7 kHz. The spectrum, expanded from 0 ppm-7 ppm, is depicted in FIG. 20. A Fourier Transform of the proton MAS NMR spectrum was performed by commercial NMR spectrometer computer software and analyzed by performing a standard baseline correction procedure and by providing frequency assignments of the two sharp peaks for the ethylene glycol reference standard at 5.01 ppm (hydroxyl group) and 3.73 ppm (methylene group). The difference between the two frequencies (Δν=511.51 Hz, as shown in FIG. 20) was used as a numerical input to calculate, using an equation known in the art (e.g., *J. Magn. Reson.* 1982, 46, 319-321, incorporated by reference herein), the absolute temperature in Kelvins of the target sample material of the rubber band sample. As can be seen in FIG. 20, the absolute temperature of the rubber band sample was 336.065K. The absolute temperature and proton MAS NMR spectral features (peak positions, shapes, etc.) of the target sample material in the unknown sample constitutes unique and specific data that was used to characterize and define the target sample material in the unknown sample. It is well known in the art that the chemical shifts and widths for peaks in the proton NMR spectra of materials change as a function of temperature and in doing so reveal the specific molecular dynamics that the materials undergo. Molecular dynamics information is useful for characterizing the dynamic architecture of materials and is used to explain the physical properties of polymer materials.

What is claimed is:

1. A method for performing one or more quantitative measurements of a target sample using solid state Magic Angle Spinning (MAS) Nuclear Magnetic Resonance (NMR) spectroscopy, the method comprising:
providing an in situ measuring device, the in situ measuring device comprising a solid state MAS NMR rotor and at least one sealed capillary tube positioned inside the solid state MAS NMR rotor, the at least one sealed capillary tube having a reference material sealed inside the at least one capillary tube between first and second fused glass ends of the at least one sealed capillary tube, wherein a target sample is positioned on the inside of the solid state MAS NMR rotor, and wherein a first portion of the target sample is in contact with an inner surface of the solid state MAS NMR rotor and a second portion of the target sample is in contact with an outer surface of the at least one sealed capillary tube;
obtaining MAS NMR spectra of the target sample and the reference material; and
determining one or more quantitative properties of the target sample, the one or more quantitative properties comprising one or more of a quantity of the target sample, a chemical identity of the target sample, or a temperature of the target sample.

2. The method of claim 1, wherein the reference material comprises one or more of ethylene glycol, methanol, ethanol, water, or mixtures thereof.

3. The method of claim 1, wherein the at least one sealed capillary tube comprises a plurality of sealed capillary tubes, wherein each of the plurality of sealed capillary tubes are positioned inside the solid state MAS NMR rotor.

4. The method of claim 3, wherein each of the plurality of sealed capillary tubes has the same reference material sealed inside.

5. The method of claim 1, wherein the obtaining MAS NMR spectra of the target sample and the reference material comprises simultaneously obtaining the MAS NMR spectra of the target sample and the reference material.

6. The method of claim 1, wherein the one or more quantitative properties comprises the chemical identity of the target sample.

7. The method of claim 1, wherein the one or more quantitative properties comprises the quantity of the target sample.

8. The method of claim 1, wherein the one or more quantitative properties comprises the temperature of the target sample.

9. The method of claim 1, wherein the at least one sealed capillary tube has an outer diameter less than 600 micrometers.

10. A method for performing one or more quantitative measurements of a target sample using solid state Magic Angle Spinning (MAS) Nuclear Magnetic Resonance (NMR) spectroscopy, the method comprising:
providing an in situ measuring device, the in situ measuring device comprising a solid state MAS NMR rotor and at least one sealed capillary tube positioned inside the solid state MAS NMR rotor, the at least one sealed capillary tube having a reference material sealed inside the at least one capillary tube between first and second fused glass ends of the at least one sealed capillary tube, wherein a target sample is positioned on the inside of the solid state MAS NMR rotor, and wherein a first portion of the target sample is in contact with an inner surface of the solid state MAS NMR rotor and a second portion of the target sample is in contact with an outer surface of the at least one sealed capillary tube;
inserting the in situ measuring device inside a probe of a solid state MAS NMR instrument,
while the in situ measuring device is positioned inside a probe of a solid state MAS NMR instrument, obtaining MAS NMR spectra of the target sample and the reference material, wherein at least one MAS NMR spectra peak associated with the reference material is spaced apart from at least one MAS NMR spectra peak associated with the target material; and determining one or more of a quantity of the target sample or a chemical identity of the target sample based on the MAS NMR spectra of the target sample and the reference material.

11. The method of claim 10, wherein the reference material comprises one or more of ethylene glycol, methanol, ethanol, water, or mixtures thereof.

12. The method of claim 10, wherein the obtaining MAS NMR spectra of the target sample and the reference material comprises recording the solid state MAS NMR spectra using a Bloch decay pulse sequence.

13. The method of claim 10, wherein the at least one sealed capillary tube has an outer diameter less than 600 micrometers.

14. A method for forming an in situ measuring device for solid state Magic Angle Spinning (MAS) Nuclear Magnetic Resonance (NMR) spectroscopy, the method comprising:
providing at least one capillary tube;
adding at least one reference material to an inside cavity of the at least one capillary tube;
sealing the at least one capillary tube by fusing glass at a first end and a second end to form at least one sealed capillary tube having the at least one reference material sealed inside;
providing a solid state MAS NMR rotor, the solid state MAS NMR rotor configured to house a target sample;
positioning the at least one sealed capillary tube inside the solid state MAS NMR rotor; and
adding at least one target material to the interior of the solid state MAS NMR rotor such that at least a portion of the target material is in contact with an inner surface of the solid state MAS NMR rotor and at least another portion of the target material is in contact with an outer surface of the at least one sealed capillary tube.

15. The method of claim 14, wherein the sealing the at least one capillary tube is performed using a micro torch.

16. The method of claim 14, wherein the at least one capillary tube is coupled to a foundation member at one end of the at least capillary tube.

17. The method of claim 16, wherein the positioning the at least one sealed capillary tube inside the solid state MAS NMR rotor comprises positioning the foundation member adjacent to a bottom inner surface of the solid state MAS NMR rotor.

18. The method of claim 14, wherein the at least one sealed capillary tube is positioned in the center of the solid state MAS NMR rotor.

19. The method of claim 14, wherein the at least one sealed capillary tube comprises a plurality of sealed capillary tubes.

20. The method of claim 14, wherein the at least one sealed capillary tube has an outer diameter that is less than 600 micrometers.

* * * * *